United States Patent
Mujkic et al.

(10) Patent No.: US 9,867,771 B2
(45) Date of Patent: *Jan. 16, 2018

(54) WAXES DERIVED FROM METATHESIZED NATURAL OILS AND AMINES AND METHODS OF MAKING

(71) Applicant: Elevance Renewable Sciences, Inc., Woodridge, IL (US)

(72) Inventors: Monika Mujkic, Pendleton, SC (US); Deidra Cade, Pendleton, SC (US); Choon Woo Lee, Pasadena, CA (US); Michael S. Starch, Midland, MI (US); Brian J. Swanton, Midland, MI (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/012,307

(22) Filed: Feb. 1, 2016

(65) Prior Publication Data

US 2016/0317428 A1    Nov. 3, 2016

Related U.S. Application Data

(63) Continuation of application No. 13/176,851, filed on Jul. 6, 2011, now Pat. No. 9,249,360.

(Continued)

(51) Int. Cl.
*A61K 8/92* (2006.01)
*C08L 91/06* (2006.01)
(Continued)

(52) U.S. Cl.
CPC ............ *A61K 8/922* (2013.01); *A61Q 1/06* (2013.01); *A61Q 5/00* (2013.01); *A61Q 17/04* (2013.01);
(Continued)

(58) Field of Classification Search
None
See application file for complete search history.

(56) References Cited

U.S. PATENT DOCUMENTS 1,935,946 A    11/1933 Egan et al.
1,954,659 A    4/1934 Will
(Continued)

FOREIGN PATENT DOCUMENTS

DE    19956226    5/2001
EP    0536861 A1    4/1993
(Continued)

OTHER PUBLICATIONS

Behren et al., "Beeswax and other Non-Paraffin Waxes," Presnted at NCA Technical Meeting, Jun. 19-20, 1991, 6 pages.
(Continued)

*Primary Examiner* — Kathrien Cruz
*Assistant Examiner* — Andrew Lee
(74) *Attorney, Agent, or Firm* — Kilpatrick Townsend & Stockton LLP

(57) ABSTRACT

Wax compositions derived from metathesized natural oils and amines and methods of making wax compositions from metathesized natural oils and amines are provided. The wax compositions comprise amidated metathesized natural oils formed from a metathesized natural oil and at least one amine. The methods comprise providing an amine and providing a metathesized natural oil. The methods further comprise mixing the amine and the metathesized natural oil in the presence of a basic catalyst or heat, causing a reaction between the amine and metathesized natural oil, therein forming the amidated metathesized natural oil.

20 Claims, 6 Drawing Sheets

Needle penetration for amidated methathesized natural oil composition as a function of reaction time.

Related U.S. Application Data

(60) Provisional application No. 61/363,016, filed on Jul. 9, 2010.

(51) Int. Cl.
  *C10G 3/00* (2006.01)
  *A61Q 19/00* (2006.01)
  *A61Q 1/06* (2006.01)
  *A61Q 5/00* (2006.01)
  *A61Q 17/04* (2006.01)

(52) U.S. Cl.
  CPC ............ *A61Q 19/00* (2013.01); *A61Q 19/007* (2013.01); *C08L 91/06* (2013.01); *C10G 3/00* (2013.01); *A61K 2800/10* (2013.01); *C10G 2300/1014* (2013.01); *C10G 2300/1018* (2013.01); *C10G 2300/20* (2013.01); *C10G 2300/202* (2013.01); *Y02P 30/20* (2015.11)

(56) References Cited

U.S. PATENT DOCUMENTS

| | | |
|---|---|---|
| 2,468,799 A | 5/1949 | Ziels et al. |
| 2,784,891 A | 3/1957 | Thielke |
| 3,448,178 A | 6/1969 | Flanagan |
| 3,630,697 A | 12/1971 | Duling et al. |
| 3,645,705 A | 2/1972 | Miller et al. |
| 3,744,956 A | 7/1973 | Hess |
| 3,844,706 A | 10/1974 | Tsaras |
| 4,118,203 A | 10/1978 | Beardmore et al. |
| 4,134,718 A | 1/1979 | Kayfetz et al. |
| 4,292,088 A | 9/1981 | Scheuffgen et al. |
| 4,293,345 A | 10/1981 | Zeilstra et al. |
| 4,314,915 A | 2/1982 | Wiegers et al. |
| 4,390,590 A | 6/1983 | Saunders et al. |
| 4,411,829 A | 10/1983 | Schulte-Elte et al. |
| 4,434,306 A | 2/1984 | Kobayashi et al. |
| 4,507,077 A | 3/1985 | Sapper |
| 4,545,941 A | 10/1985 | Rosenburg |
| 4,554,107 A | 11/1985 | Takao |
| 4,567,548 A | 1/1986 | Schneeberger |
| 4,608,011 A | 8/1986 | Comstock |
| 4,614,625 A | 9/1986 | Wilson |
| 4,623,488 A | 11/1986 | Takao |
| 4,714,496 A | 12/1987 | Luken, Jr. et al. |
| 4,759,709 A | 7/1988 | Luken, Jr. et al. |
| 4,813,975 A | 3/1989 | Poulina et al. |
| 4,842,648 A | 6/1989 | Phadoemchit et al. |
| 4,855,098 A | 8/1989 | Taylor |
| 4,923,708 A | 5/1990 | Given, Jr. |
| 5,171,329 A | 12/1992 | Lin |
| 5,258,197 A | 11/1993 | Wheeler et al. |
| 5,338,187 A | 8/1994 | Elharar |
| 5,378,452 A | 1/1995 | Greczyn |
| 5,380,544 A | 1/1995 | Klemann et al. |
| 5,578,089 A | 11/1996 | Elsamaloty |
| 5,660,865 A | 8/1997 | Pedersen et al. |
| 5,700,516 A | 12/1997 | Sandvick et al. |
| 5,723,137 A | 3/1998 | Wahle et al. |
| 5,753,015 A | 5/1998 | Sinwald et al. |
| 5,843,194 A | 12/1998 | Spaulding |
| 5,885,600 A | 3/1999 | Blum et al. |
| 5,888,487 A | 3/1999 | Baumoeller et al. |
| 6,001,286 A | 12/1999 | Sleeter |
| 6,019,804 A | 2/2000 | Requejo et al. |
| 6,022,402 A | 2/2000 | Stephenson et al. |
| 6,063,144 A | 5/2000 | Calzada et al. |
| 6,099,877 A | 8/2000 | Schuppan |
| 6,103,308 A | 8/2000 | Floyd et al. |
| 6,106,597 A | 8/2000 | Starks et al. |
| 6,123,979 A | 9/2000 | Hepburn et al. |
| 6,127,326 A | 10/2000 | Dieckmann et al. |
| 6,132,742 A | 10/2000 | Le Bras et al. |
| 6,156,369 A | 12/2000 | Eger et al. |
| 6,201,053 B1 | 3/2001 | Dieckmann et al. |
| 6,211,315 B1 | 4/2001 | Larock et al. |
| 6,214,918 B1 | 4/2001 | Johnson et al. |
| 6,224,641 B1 | 5/2001 | Matzat et al. |
| 6,238,926 B1 | 5/2001 | Liu et al. |
| 6,255,375 B1 | 7/2001 | Michelman |
| 6,258,965 B1 | 7/2001 | O'Lenick, Jr. |
| 6,262,153 B1 | 7/2001 | Webster et al. |
| 6,276,925 B1 | 8/2001 | Varga |
| 6,277,310 B1 | 8/2001 | Sleeter |
| 6,284,007 B1 | 9/2001 | Tao |
| 6,316,545 B1 | 11/2001 | Sakuta |
| 6,497,735 B2 | 12/2002 | Tao |
| 6,503,077 B2 | 1/2003 | Orth et al. |
| 6,503,285 B1 | 1/2003 | Murphy |
| 6,582,748 B1 | 6/2003 | Loh et al. |
| 6,586,506 B2 | 7/2003 | Webster et al. |
| 6,599,334 B1 | 7/2003 | Anderson |
| 6,645,261 B2 | 11/2003 | Murphy et al. |
| 6,673,763 B1 | 1/2004 | Hansen et al. |
| 6,730,137 B2 | 5/2004 | Pesu et al. |
| 6,733,548 B2 | 5/2004 | Rasmussen et al. |
| 6,758,869 B2 | 7/2004 | Roeske et al. |
| 6,770,104 B2 | 8/2004 | Murphy |
| 6,773,469 B2 | 8/2004 | Murphy |
| 6,797,020 B2 | 9/2004 | Murphy |
| 6,824,572 B2 | 11/2004 | Murphy |
| 6,846,573 B2 | 1/2005 | Seydel |
| 6,852,140 B1 | 2/2005 | Roeske |
| 6,943,262 B2 | 9/2005 | Kodali et al. |
| 7,037,439 B2 | 5/2006 | Tavares |
| 7,128,766 B2 | 10/2006 | Murphy et al. |
| 7,176,171 B2 | 2/2007 | Nieendick et al. |
| 7,192,457 B2 | 3/2007 | Murphy et al. |
| 7,217,301 B2 | 5/2007 | Murphy et al. |
| 7,387,649 B2 | 6/2008 | Tao |
| 7,462,205 B2 | 12/2008 | Murphy |
| 7,510,584 B2 | 3/2009 | Cap |
| 7,569,084 B2 | 8/2009 | Tao et al. |
| 7,588,607 B1 | 9/2009 | Cap |
| 7,601,184 B2 | 10/2009 | Tischendorf |
| 7,637,968 B2 | 12/2009 | Murphy |
| 2001/0013195 A1 | 8/2001 | Tao |
| 2001/0051680 A1 | 12/2001 | Webster et al. |
| 2002/0005007 A1 | 1/2002 | Roeske et al. |
| 2002/0144455 A1 | 10/2002 | Bertrand et al. |
| 2002/0157303 A1 | 10/2002 | Murphy et al. |
| 2003/0008257 A1 | 1/2003 | Tao |
| 2003/0017431 A1 | 1/2003 | Murphy |
| 2003/0022121 A1 | 1/2003 | Biggs |
| 2003/0046860 A1 | 3/2003 | Tiffany et al. |
| 2003/0057599 A1 | 3/2003 | Murphy et al. |
| 2003/0061760 A1 | 4/2003 | Tao et al. |
| 2003/0091949 A1 | 5/2003 | Pesu et al. |
| 2003/0110683 A1 | 6/2003 | Murphy |
| 2003/0134244 A1 | 7/2003 | Gray et al. |
| 2003/0198826 A1 | 10/2003 | Seydel |
| 2003/0207971 A1 | 11/2003 | Stuart, Jr. et al. |
| 2003/0213163 A1 | 11/2003 | Berger et al. |
| 2004/0000088 A1 | 1/2004 | Wesley |
| 2004/0037859 A1 | 2/2004 | Cecchi et al. |
| 2004/0047886 A1 | 3/2004 | Murphy et al. |
| 2004/0076732 A1 | 4/2004 | Valix |
| 2004/0088907 A1 | 5/2004 | Murphy |
| 2004/0088908 A1 | 5/2004 | Murphy |
| 2004/0138359 A1 | 7/2004 | Dinkelaker et al. |
| 2004/0200136 A1 | 10/2004 | Tao et al. |
| 2004/0221503 A1 | 11/2004 | Murphy et al. |
| 2004/0221504 A1 | 11/2004 | Murphy |
| 2005/0014664 A1 | 1/2005 | Nadolsky et al. |
| 2005/0060927 A1 | 3/2005 | Murphy |
| 2005/0095545 A1 | 5/2005 | Tischendorf |
| 2005/0123780 A1 | 6/2005 | Seydel |
| 2005/0158679 A1 | 7/2005 | Chen et al. |
| 2005/0269728 A1 | 12/2005 | Roos |
| 2006/0088493 A1 | 4/2006 | Vic et al. |
| 2006/0236593 A1 | 10/2006 | Cap |
| 2006/0272199 A1 | 12/2006 | Licciardello et al. |
| 2006/0272200 A1 | 12/2006 | Murphy et al. |
| 2007/0006521 A1 | 1/2007 | Licciardello et al. |

(56) References Cited

U.S. PATENT DOCUMENTS

| | | |
|---|---|---|
| 2007/0006522 A1 | 1/2007 | Tao |
| 2007/0039237 A1 | 2/2007 | Murphy et al. |
| 2007/0056211 A1 | 3/2007 | Li et al. |
| 2007/0144058 A1 | 6/2007 | Chen et al. |
| 2007/0151480 A1 | 7/2007 | Bloom et al. |
| 2007/0270621 A1 | 11/2007 | Millis et al. |
| 2007/0282000 A1 | 12/2007 | Murphy et al. |
| 2008/0027194 A1 | 1/2008 | Schrodi |
| 2008/0064891 A1 | 3/2008 | Lee |
| 2008/0138753 A1 | 6/2008 | Tao et al. |
| 2008/0145808 A1 | 6/2008 | Lee |
| 2008/0206411 A1 | 8/2008 | Nielsen |
| 2008/0307696 A1 | 12/2008 | Wu et al. |
| 2009/0043140 A1 | 2/2009 | Yang et al. |
| 2009/0048459 A1 | 2/2009 | Tupy et al. |
| 2009/0119977 A1 | 5/2009 | Murphy |
| 2009/0217568 A1 | 9/2009 | Murphy et al. |
| 2009/0259065 A1 | 10/2009 | Abraham et al. |
| 2009/0264672 A1 | 10/2009 | Abraham et al. |
| 2010/0024281 A1 | 2/2010 | Lemke et al. |
| 2010/0044924 A1 | 2/2010 | Cap |
| 2010/0047499 A1 | 2/2010 | Braksmayer et al. |
| 2010/0132250 A1 | 6/2010 | Uptain et al. |
| 2010/0145086 A1 | 6/2010 | Schrodi et al. |
| 2010/0205851 A1 | 8/2010 | Uptain et al. |

FOREIGN PATENT DOCUMENTS

| | | | |
|---|---|---|---|
| EP | 0545715 A1 | | 6/1993 |
| EP | 0685554 A1 | | 12/1995 |
| EP | 0811664 A1 | | 12/1997 |
| EP | 1693436 A1 | | 8/2006 |
| EP | 1696022 A1 | | 8/2006 |
| EP | 1801096 A1 | | 6/2007 |
| JP | 56-32550 A | | 4/1981 |
| JP | 04-59897 A | | 2/1992 |
| JP | 06-009987 A | | 1/1994 |
| JP | 09-014574 A | | 1/1997 |
| WO | WO 92/000269 | | 1/1992 |
| WO | WO 96/00815 A1 | | 1/1996 |
| WO | WO 96/14373 A1 | | 5/1996 |
| WO | WO 98/45390 A1 | | 10/1998 |
| WO | WO 99/27043 A1 | | 6/1999 |
| WO | WO 02/030386 A1 | | 4/2002 |
| WO | WO 02/092736 A1 | | 11/2002 |
| WO | WO 03/012016 A1 | | 2/2003 |
| WO | WO 03/051134 A2 | | 6/2003 |
| WO | WO 03/057983 A1 | | 7/2003 |
| WO | WO 03/104348 A1 | | 12/2003 |
| WO | WO 2004/033388 A1 | | 4/2004 |
| WO | WO 2004/083310 A1 | | 9/2004 |
| WO | WO 2004/101720 A1 | | 11/2004 |
| WO | WO 2005/042655 A2 | | 5/2005 |
| WO | WO 2006/041011 A1 | | 4/2006 |
| WO | WO 2006/076364 A2 | | 7/2006 |
| WO | WO 2007/002999 A1 | | 1/2007 |
| WO | WO 2007/103398 | | 9/2007 |
| WO | WO 2008/008420 A1 | | 1/2008 |
| WO | WO 2008/010961 A2 | | 1/2008 |
| WO | WO 2008/048520 A2 | | 4/2008 |
| WO | WO 2008/103289 A1 | | 8/2008 |
| WO | WO 2008/140468 A2 | | 11/2008 |
| WO | WO 2008/151064 A1 | | 12/2008 |
| WO | WO 2008/157436 A1 | | 12/2008 |
| WO | WO 2009/053594 | | 4/2009 |

OTHER PUBLICATIONS

Bell et al., "Sperm Oil Replacements: Synthetic Wax Esters from Selectively Hydrogenated Soybean and Linseed Oils," Journal of the American Chemical Society, Jun. 1997, vol. 54, pp. 259-263.

Erhan et al., "Drying Properties of Metathesized Soybean Oil," Journal of American Oil Chemists' Society, AOCS Press, vol. 74, No. 6, 1997, pp. 703-706.

Frahm, "Harvest Lights: The only soy-based candle, a bright idea," available at http://www.extension.uiuc.edu/~stratsoy/new/news/html/909166253,html, Oct. 23, 1998, 2 pages.

Mol, "Applications of Olefin Metathesis in Oleochemistry: An Example of Green Chemistry," Green Chemistry, Royal Society of Chemistry, Cambridge, GB, vol. 4, 2002, pp. 5-13.

Noller, Chemistry of Organic Compounds, W.B. Saunders Company, $2^{nd}$ Ed., 1957, pp. 181 and 192.

Oliefabrik et al., "Paper coating", Research Disclosure Journal, Dec. 1996, 2 pages.

Orso, "New Use for Soybeans Has Bright Future," available at http://www.unitedsoybean.com/news/nr981014.htm, Oct. 14, 1998, 2 pages.

Rezaei, "Hydrogenated Vegetable Oils as Candle Wax," J. of the Am. Oil Chemists' Society, vol. 12, No. 79, pp. 1241-1247 (Dec. 2002).

Tao, "Development of Vegetable Lipid-based Candles," available at http://abe.www.ecn.purdue.edu/ABE/Research/research94/RE-PORT.94.Book_68.htmls, 1994, 2 pages.

In Business, "America's Shining Example of Sustainable Business," available at http://www.candleworks.org, Mar./Apr. 1998, 3 pages.

Pages from Bitter Creek Candle Supply, Inc., website (http://www.execpc.com/~bcsupply) now at http://www.candlesupply.com, available at least by Jun. 29, 2000, 9 pages.

Pages from Ecowax, Nature's Gift, Inc., website (http://nglwax.com/ecowax.htm), available at least by Jul. 5, 2000, 3 pages.

Pages from Heartland Candleworks website, available at www.candleworks.org, available at least by Feb. 11, 2000, 4 pages.

Purdue Agriculture News, Purdue May Agriculture & Natural Resources Package, available at http://purduenews.uns.purdue.edu/UNS/paks/agpak.digest.9605.html, May 1996, 3 pages.

Purdue News, "Purdue students put the 'happy' back into birthday candles," available at http://www.purdue.edu/UNS/html4ever/9611.Schweitzer.candles.html, Nov. 1996, 3 pages.

Purdue News, "Purdue students put the 'happy' back into birthday candles," available at http://www.purdue.edu/UNS/html4ever/9604.Schweitzer.candles.html, May 1996, 2 pages.

Purdue University School of Agriculture, 1998 Farm Progress Show, available at http://www.admin.ces.purdue.edu/anr/98fps/fpspix/930.html, 1998, 4 pages.

Office Action, Chinese Patent App. No. 201180034116.1, dated May 26, 2014.

Nippon Seika, http://www.nipponseika.co.jp/eng/industry/polylefins103.htm, accessed May 2, 2013, publication dated Aug. 21, 2007.

Figure 1. Metathesis reaction scheme of a natural oil.

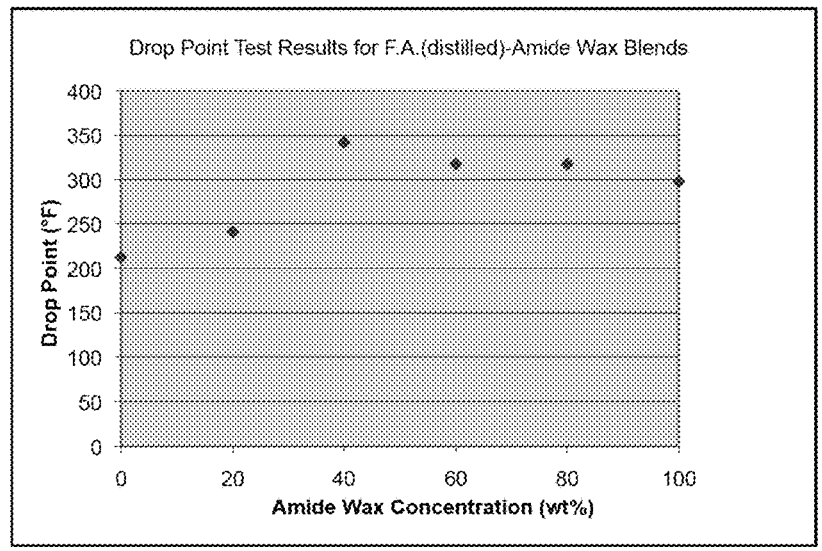
Figure 4. Drop points for fatty acid-amidated methathesized natural oil blends for various concentrations of amide wax.
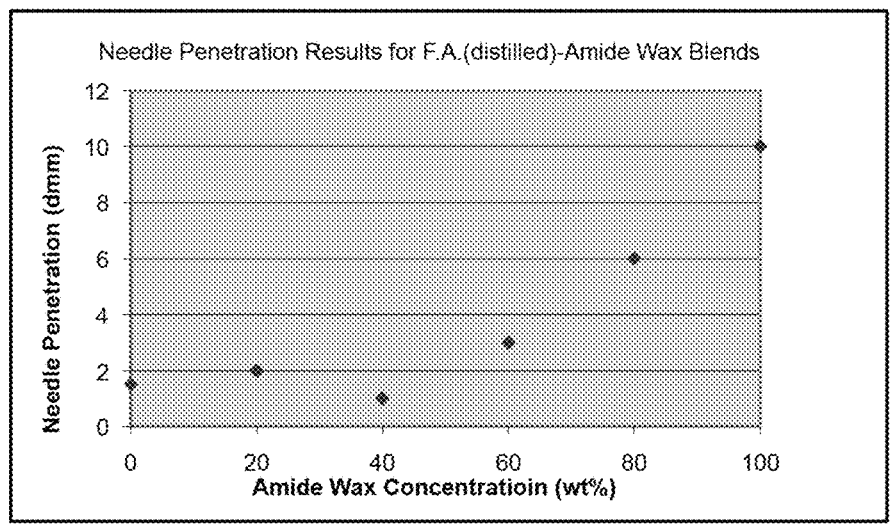
Figure 5. Needle penetration values for the fatty acid-amidated methathesized natural oil blends.

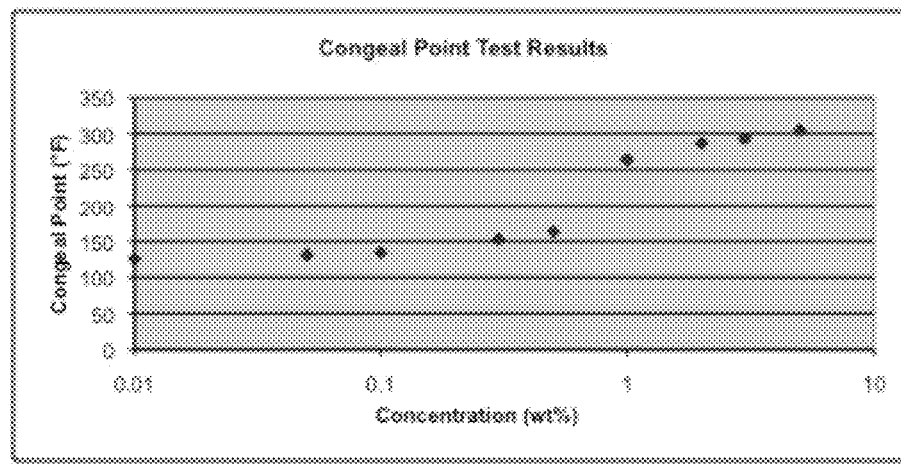
Figure 6. Congeal points for S155-amidated methathesized natural oil blends for various concentrations of amidated methathesized natural oil.
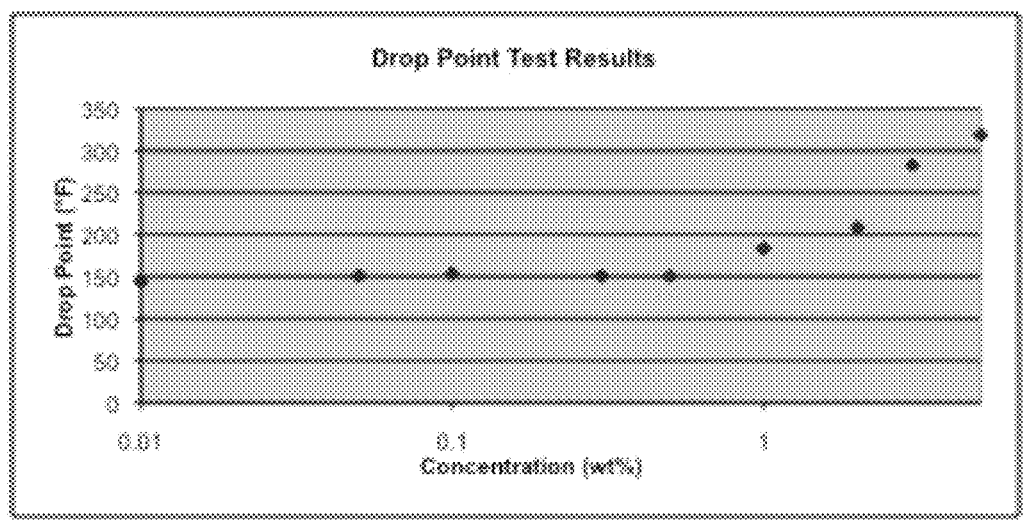
Figure 7. Drop points for S155-amidated methathesized natural oil blends (HMSBO+ethylenediame) for various concentrations of amidated methathesized natural oil.

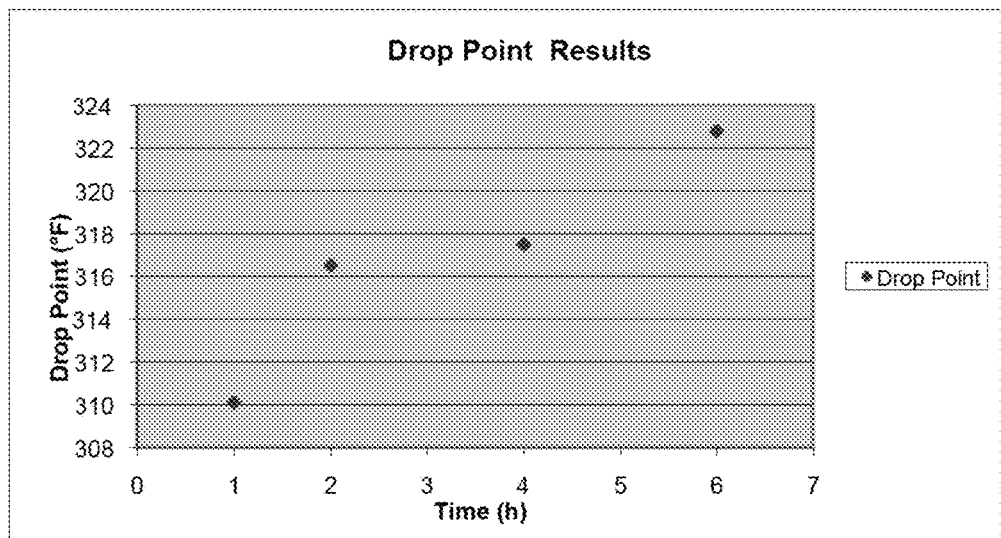
Figure 8. Drop point for amidated methathesized natural oil composition as a function of reaction time.
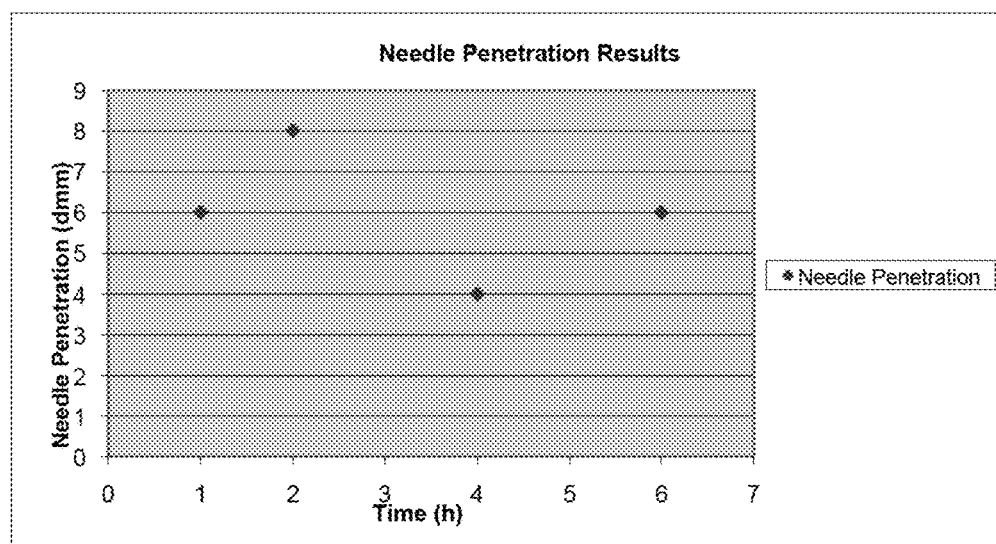
Figure 9. Needle penetration for amidated methathesized natural oil composition as a function of reaction time.

WAXES DERIVED FROM METATHESIZED NATURAL OILS AND AMINES AND METHODS OF MAKING

CROSS REFERENCE TO RELATED APPLICATIONS

This application is a continuation of U.S. patent application Ser. No. 13/176,851, filed Jul. 6, 2011, which claims the benefit of U.S. Provisional Application No. 61/363,016, filed Jul. 9, 2010, both of which are hereby incorporated by reference as though set forth herein in their entirety.

BACKGROUND

Metathesis is a catalytic reaction generally known in the art that involves the interchange of alkylidene units among compounds containing one or more double bonds (e.g., olefinic compounds) via the formation and cleavage of the carbon-carbon double bonds. Metathesis may occur between two like molecules (often referred to as self-metathesis) and/or it may occur between two different molecules (often referred to as cross-metathesis). Self-metathesis may be represented schematically as shown in Equation I.

$$R^1-CH=CH-R^2+R^1-CH=CH-R^2 \leftrightarrow R^1-CH=CH-R^1+R^2-CH=CH-R^2 \quad (I)$$

wherein $R^1$ and $R^2$ are organic groups.

Cross-metathesis may be represented schematically as shown in Equation II.

$$\begin{aligned}R^1-CH=CH-R^2+R^3-CH=CH-R^4 &\leftrightarrow R^1-CH=CH-R^3+R^1-CH=CH-R^4+R^2-\\&\phantom{\leftrightarrow} CH=CH-R^3+R^2-CH=CH-R^4+R^1-\\&\phantom{\leftrightarrow} CH=CH-R^1+R^2-CH=CH-R^2+R^3-\\&\phantom{\leftrightarrow} CH=CH-R^3+R^4-CH=CH-R^4\end{aligned} \quad (II)$$

wherein $R^1$, $R^2$, $R^3$, and $R^4$ are organic groups.

In recent years, there has been an increased demand for environmentally friendly techniques for manufacturing materials to take the place of materials typically derived from petroleum sources. For example, researchers have been studying the feasibility of manufacturing biofuels, waxes, plastics, and the like, using natural oil feedstocks, such as vegetable and seed-based oils. In one non-limiting example, metathesis catalysts are used to manufacture candle wax, as described in PCT/US2006/000822, which is herein incorporated by reference. Metathesis reactions involving natural oil feedstocks offer promising solutions for today and for the future.

The metathesized natural oil-based compositions may have low melting points that are suitable for use in certain applications, such as candle waxes. However, it would be advantageous to develop higher melting point waxes that utilize the metathesized natural oil as well. Such waxes would have the potential to replace microcrystalline polyethylene or Fisher-Tropsch based waxes. Additionally, higher melting point waxes could used as a structuring agent in cosmetics, emulsifying/thickening agent, slip agent, internal lubricant, pigment dispersant, or a hot melt adhesive, as well as other wax applications.

BRIEF SUMMARY

Compositions and related methods of making are disclosed for waxes derived from metathesized natural oils and amines.

In one embodiment, the wax composition comprises an amidated metathesized natural oil formed from a metathesized natural oil and at least one amine, wherein the amidated metathesized natural oil comprises molecules having the following structures:

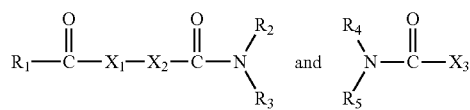

wherein $R_1$ is selected from the group consisting of:

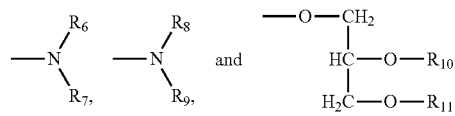

wherein $R_2$, $R_3$, $R_4$, $R_5$, $R_6$, $R_7$, $R_8$, and $R_9$ are independently selected from the group consisting of hydrogen, alcohols, alkyls, aryls, alkyl-amines, aryl-amines, ether amines, amino acids and esters, thiol amines, ureas, and thioureas, wherein $R_{10}$ and $R_{11}$ are independently selected from the group consisting of:

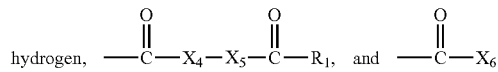

wherein $X_1$, $X_2$, $X_3$, $X_4$, $X_5$, and $X_6$ are independently selected from the group consisting of $C_4$-$C_{28}$ saturated or unsaturated alkyl chains from either a fatty acid of a natural oil, or a derivative thereof formed by a metathesis reaction.

In certain embodiments, the metathesized natural oil is a hydrogenated metathesized natural oil. In some embodiments, the hydrogenated metathesized natural oil is fully hydrogenated.

In certain embodiments, the hydrogenated metathesized natural oil is selected from the group consisting of hydrogenated metathesized vegetable oil, hydrogenated metathesized algal oil, hydrogenated metathesized animal fat, hydrogenated metathesized tall oil, hydrogenated metathesized derivatives of these oils, and mixtures thereof. In some embodiments, the hydrogenated metathesized natural oil is selected from the group consisting of hydrogenated metathesized vegetable oil is hydrogenated metathesized canola oil, hydrogenated metathesized rapeseed oil, hydrogenated metathesized coconut oil, hydrogenated metathesized corn oil, hydrogenated metathesized cottonseed oil, hydrogenated metathesized olive oil, hydrogenated metathesized palm oil, hydrogenated metathesized peanut oil, hydrogenated metathesized safflower oil, hydrogenated metathesized sesame oil, hydrogenated metathesized soybean oil, hydrogenated metathesized sunflower oil, hydrogenated metathesized linseed oil, hydrogenated metathesized palm kernel oil, hydrogenated metathesized tung oil, hydrogenated metathesized jatropha oil, hydrogenated metathesized mustard oil, hydrogenated metathesized camelina oil, hydrogenated metathesized pennycress oil, hydrogenated metathesized castor oil, hydrogenated metathesized derivatives of these oils, and mixtures thereof.

In certain embodiments, the amine is selected from the group consisting of: methylamine, dimethylamine, ethylamine, diethylamine, propylamine, dipropylamine, butylamine, dibutylamine, pentylamine, dipentylamine, hexylamine, dihexylamine, heptylamine, diheptylamine, octylamine, dioctylamine, methanolamine, dimethanolamine, ethanolamine, diethanolamine, propanolamine, dipropanolamine, butanolamine, dibutanolamine, pentanolamine, dipentanolamine, hexanolamine, dihexanolamine, heptanolamine, diheptanolamine, octanolamine, dioctanolamine, aniline, ethylenediamine (1,2-ethanediamine), 1,3-propanediamine, 1,4-butanediamine (putrescine), 1,5-pentanediamine, 1,6-hexanediamine, 1,7-heptanediamine, 1,8-octanediamine, 1,3-bis(aminomethyl)cyclohexane, meta-xylenediamine, 1,8-naphthalenediamine, p-phenylenediamine, N-(2-aminoethyl)-1,3-propanediamine, diethylenetriamine, dipropylenetriamine, dibutylenetriamine, dipentylenetriamine, dihexylenetriamine, diheptylenetriamine, dioctylenetriamine, spermidine, melamine, triethylenetetramine, tripropylenetetramine, tributylenetetramine, tripentylenetetramine, trihexylenetetramine, triheptylenetetramine, trioctylenetetramine, hexamine, imidazole, or oxazolidine, and mixtures thereof. In other embodiments, the amine is selected from the group consisting of amino acids or esters, ureas, thiol amines, ether amines, and mixtures thereof.

In some embodiments, the amine is a polar amine and the amidated metathesized natural oil is a hydrous amidated metathesized natural oil. In other embodiments, the amine is a non-polar amine and the amidated metathesized natural oil is an anhydrous amidated metathesized natural oil.

In certain embodiments, the wax composition comprises a drop point between 70° C. and 200° C., and a hardness between 1 dmm and 40 dmm as measured by needle penetration. In some embodiments, the amidated metathesized natural oil composition has a drop point that is greater by at least 10° C. than the drop point of a second metathesized natural oil composition similar in all respects except that the second metathesized natural oil composition is not amidated.

In certain embodiments, the amidated metathesized natural oil is blended with a natural oil composition to form an amidated metathesized natural oil-natural oil blend; wherein the amidated metathesized natural oil comprises between 0.1 percent by weight and 10 percent by weight of the wax composition; wherein the drop point of the amidated metathesized natural oil-natural oil blend is greater than the drop point of the natural oil composition by at least 5° C.

In certain embodiments, the wax is used in an application selected from the group consisting of: a high temperature lubricant, a rheology modifier, a plastic processing application, a polymer processing application, a wood/plastic composite application, a hot melt adhesive application, a metal working application, a road construction wax application, an emulsifying wax application, a binder for cosmetics, a hardness modifier application, a thickening agent application, a metal powder processing application, a wetting agent application, a foam stabilizer application, a polish application, a coating application, a structurant application, a structurant or nucleating agent for a cosmetic or adhesive application, a pigment carrier application, a corrosion inhibitor application, a clarifying agent application, an ink/toner application, a sunscreen application, a lip balm application, a lipstick application, a sunscreen stick application, a hair pomade application, hand/body lotion application, or a leveling agent for an anticorrosion application. In some embodiments, the wax composition has between 1 percent by weight and 15 percent by weight amidated metathesized natural oil in the application.

In another embodiment, the wax composition further comprises a hydroxy-metathesis oligomer having the following structure:

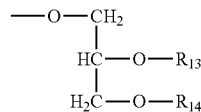

wherein $R_{12}$ is:

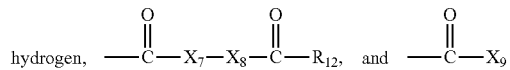

wherein $R_{13}$ and $R_{14}$ are independently selected from the group consisting of:

$$\text{hydrogen,} \quad -\overset{O}{\underset{\|}{C}}-X_7-X_8-\overset{O}{\underset{\|}{C}}-R_{12}, \quad \text{and} \quad -\overset{O}{\underset{\|}{C}}-X_9$$

wherein $X_7$, $X_8$, and $X_9$ are independently selected from the group consisting of $C_4$-$C_{28}$ saturated or unsaturated alkyl chains from either a fatty acid of a natural oil, or a derivative thereof formed by a metathesis reaction.

In another embodiment, a method of making an amidated metathesized natural oil comprises providing an amine and providing a metathesized natural oil. The method further comprises mixing the amine and the metathesized natural oil in the presence of a basic catalyst or heat, causing a reaction between the amine and metathesized natural oil, therein forming the amidated metathesized natural oil.

In certain embodiments, the mixing is conducted in the presence of the basic catalyst selected from the group consisting of: sodium carbonate, lithium carbonate, sodium methanolate, potassium hydroxide, sodium hydride, potassium butoxide, potassium carbonate, or a mixture thereof. In other embodiments, the mixing is conducted in an inert atmosphere.

In some embodiments, the ratio of amine equivalents in the amine to ester equivalents in the metathesized natural oil is between 1:100 and 10:1. In other embodiments, the amount of the basic catalyst is between 0.1 percent by weight and 10 percent by weight of the metathesized natural oil.

In certain embodiments, the reaction is conducted at a temperature between 80° C. and 250° C. In other embodiments, the reaction is held at the temperature for at least approximately 1 hour and less than approximately 24 hours. In yet other embodiments, the reaction is held at the temperature for less than approximately 6 hours.

In certain embodiments, the method of making the amidated metathesized natural oil further comprises vacuum-pumping the wax composition to separate at least one of the following: water, unreacted amine, glycerol, or paraffinic compounds. In other embodiments, the method of making the amidated metathesized natural oil further comprises epoxidizing the amidated metathesized natural oil with a peroxyacid.

In some embodiments, wherein the metathesized natural oil is hydrogenated before mixing with the amine.

In certain embodiments, the metathesized natural oil is selected from the group consisting of metathesized vegetable oil, metathesized algae oil, metathesized animal fat, metathesized tall oil, metathesized derivatives of these oils, and mixtures thereof. In some embodiments, the metathesized natural oil is selected from the group consisting of metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized castor oil, metathesized camelina oil, metathesized pennycress oil, metathesized derivatives of these oils, and mixtures thereof.

In certain embodiments, the amine is selected from the group consisting of: methylamine, dimethylamine, ethylamine, diethylamine, propylamine, dipropylamine, butylamine, dibutylamine, pentylamine, dipentylamine, hexylamine, dihexylamine, heptylamine, diheptylamine, octylamine, dioctylamine, methanolamine, dimethanolamine, ethanolamine, diethanolamine, propanolamine, dipropanolamine, butanolamine, dibutanolamine, pentanolamine, dipentanolamine, hexanolamine, dihexanolamine, heptanolamine, diheptanolamine, octanolamine, dioctanolamine, aniline, ethylenediamine (1,2-ethanediamine), 1,3-propanediamine, 1,4-butanediamine (putrescine), 1,5-pentanediamine, 1,6-hexanediamine, 1,7-heptanediamine, 1,8-octanediamine, 1,3-bis(aminomethyl)cyclohexane, meta-xylenediamine, 1,8-naphthalenediamine, p-phenylenediamine, N-(2-aminoethyl)-1,3-propanediamine, diethylenetriamine, dipropylenetriamine, dibutylenetriamine, dipentylenetriamine, dihexylenetriamine, diheptylenetriamine, dioctylenetriamine, spermidine, melamine, triethylenetetramine, tripropylenetetramine, tributylenetetramine, tripentylenetetramine, trihexylenetetramine, triheptylenetetramine, trioctylenetetramine, hexamine, imidazole, or oxazolidine, and mixtures thereof.

In certain embodiments, the amine is a polar amine and the amidated metathesized natural oil is a hydrous amidated metathesized natural oil. In other embodiments, the amine is a non-polar amine and the amidated metathesized natural oil is an anhydrous amidated metathesized natural oil.

In some embodiments, the amidated metathesized natural oil has a drop point between approximately 70° C. and approximately 200° C., and a hardness between approximately 1 dmm and approximately 40 dmm as measured by needle penetration. In other embodiments, the amidated metathesized natural oil has a drop point that is greater than the drop point of the metathesized natural oil by at least 10° C.

In certain embodiments, the amidated metathesized natural oil is blended with a natural oil composition to form an amidated metathesized natural oil-natural oil blend, wherein the amidated metathesized natural oil-natural oil blend has between approximately 0.1 percent by weight and approximately 10 percent by weight of the amidated metathesized natural oil; and wherein the drop point of the amidated metathesized natural oil-natural oil blend is greater than the drop point of the natural oil composition by at least 5° C.

In certain embodiments, the amidated metathesized natural oil is used in an application selected from the group consisting of: a high temperature lubricant application, a rheology modifier application, a plastic processing application, a polymer processing application, a wood/plastic composite application, a hot melt adhesive application, a metal working application, a road construction wax application, an emulsifying wax application, a binder for cosmetics, a hardness modifier application, a thickening agent application, a metal powder processing application, a wetting agent application, a foam stabilizer application, a polish application, a coating application, a structurant application, a structurant or nucleating agent for a cosmetic or adhesive application, a pigment carrier application, a corrosion inhibitor application, a clarifying agent application, an ink/toner application, a sunscreen application, a lip balm application, a lipstick application, a sunscreen stick application, a hair pomade application, a hand/body lotion application, or a leveling agent for an anticorrosion application. In some embodiments, the amidated metathesized natural oil has between approximately 1 percent by weight and 15 percent by weight amidated metathesized natural oil in the application.

BRIEF DESCRIPTION OF THE DRAWINGS

FIG. 4 depicts the drop point for fatty acid-amidated metathesized natural oil blends for various concentrations of amidated metathesized natural oil.

FIG. 5 depicts the needle penetration for fatty acid-amidated metathesized natural oil blends for various concentrations of amidated metathesized natural oil.

FIG. 6 depicts the congeal point for S155-amidated metathesized natural oil blends for various concentrations of amidated metathesized natural oil.

FIG. 7 depicts the drop point for S155-amidated metathesized natural oil blends for various concentrations of amidated metathesized natural oil.

FIG. 8 depicts the drop point for an amidated metathesized natural oil composition as a function of reaction time.

FIG. 9 depicts the needle penetration for an amidated metathesized natural oil composition as a function of reaction time.

DETAILED DESCRIPTION

Figure 1:
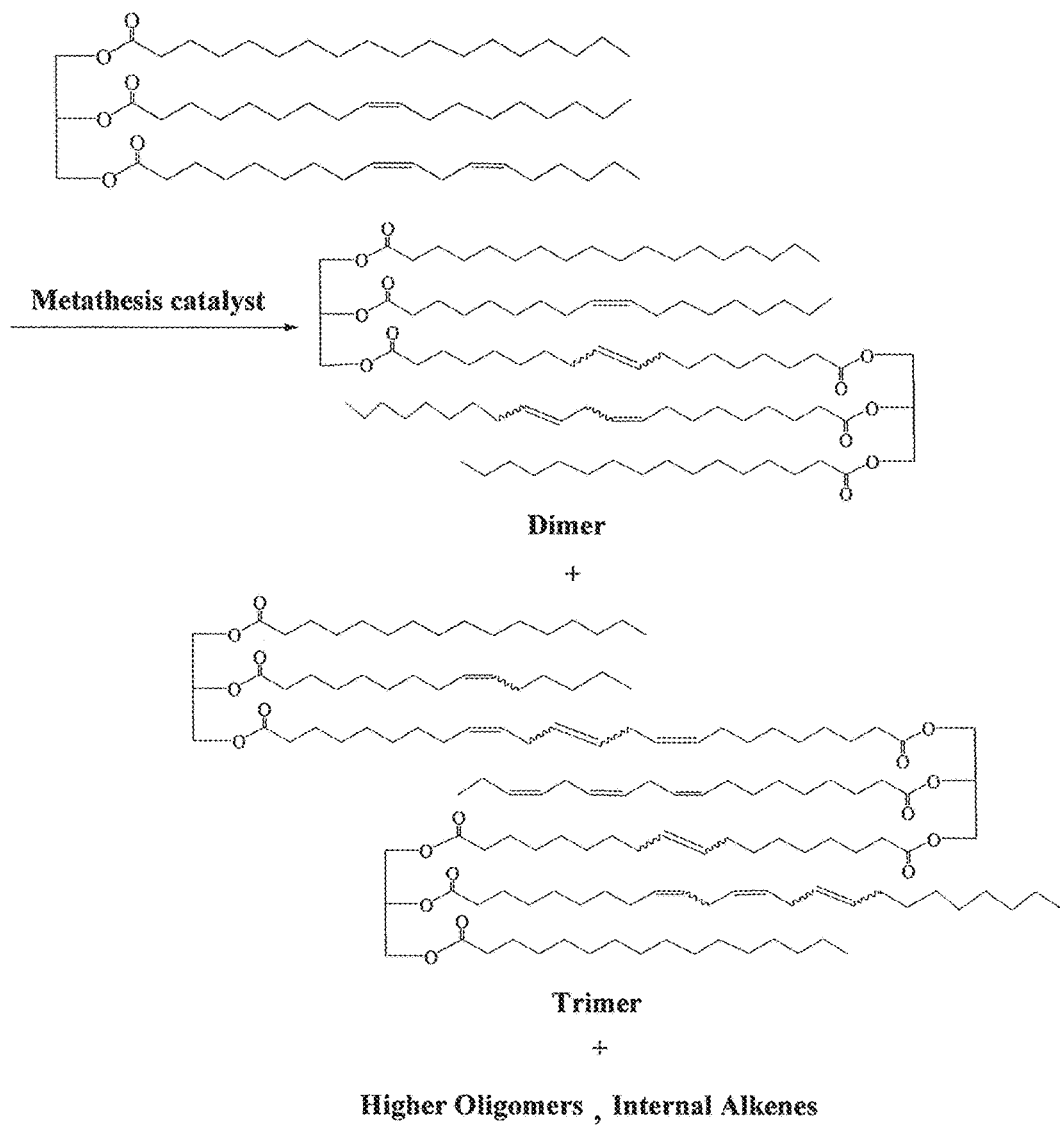
FIG. 1 depicts an exemplary metathesis reaction scheme of a natural oil.

The present application relates to wax compositions derived from natural oils and amines and methods of making wax compositions from natural oils and amines. In particular, the present application relates to wax compositions derived from metathesized natural oils and amines and methods of making wax compositions from metathesized natural oils and amines.

As used herein, the singular forms "a," "an," and "the" include plural referents unless the context clearly dictates otherwise. For example, reference to "a substituent" encompasses a single substituent as well as two or more substituents, and the like.

As used herein, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

As used herein, the following terms have the following meanings unless expressly stated to the contrary. It is understood that any term in the singular may include its plural counterpart and vice versa.

As used herein, the term "metathesis catalyst" includes any catalyst or catalyst system that catalyzes a metathesis reaction.

As used herein, the terms "natural oils," "natural feedstocks," or "natural oil feedstocks" refer to oils derived from plants or animal sources. The term "natural oil" includes natural oil derivatives, unless otherwise indicated. Examples of natural oils include, but are not limited to, vegetable oils, algal oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, and castor oil. Representative non-limiting examples of animal fats include lard, tallow, poultry fat, yellow grease, and fish oil. Tall oils are by-products of wood pulp manufacture. In certain embodiments, the natural oil may be refined, bleached, and/or deodorized.

As used herein, the term "natural oil derivatives" refers to the compounds or mixture of compounds derived from the natural oil using any one or combination of methods known in the art. Such methods include saponification, transesterification, esterification, hydrogenation (partial or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g., non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

As used herein, the terms "metathesize" and "metathesizing" may refer to the reacting of a feedstock in the presence of a metathesis catalyst to form a metathesized product or "metathesized natural oil" comprising a new olefinic compound. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming a "natural oil oligomer" having a new mixture of olefins and esters that may comprise one or more of: metathesis monomers, metathesis dimers, metathesis trimers, metathesis tetramers, metathesis pentamers, and higher order metathesis oligomers (e.g., metathesis hexamers).

As used herein, the term "metathesized natural oil" refers to the product formed from the metathesis reaction of a natural oil in the presence of a metathesis catalyst to form a mixture of olefins and esters comprising one or more of: metathesis monomers, metathesis dimers, metathesis trimers, metathesis tetramers, metathesis pentamers, and higher order metathesis oligomers (e.g., metathesis hexamers). In certain embodiments, the metathesized natural oil has been partially to fully hydrogenated, forming a "hydrogenated metathesized natural oil." In certain embodiments, the metathesized natural oil is formed from the metathesis reaction of a natural oil comprising more than one source of natural oil (e.g., a mixture of soybean oil and palm oil). In other embodiments, the metathesized natural oil is formed from the metathesis reaction of a natural oil comprising a mixture of natural oils and natural oil derivatives.

As used herein, the terms "paraffin" and "paraffins" may refer to hydrocarbon compounds having only single carbon-carbon bonds, having the general formula $C_nH_{2n+2}$.

As used herein, the term "dropping point," "drop point," or "melting point" are terms that may refer to the temperature at which the wax sample begins to melt. The drop point may be measured using ASTM-D127-08 or the Mettler Drop Point FP80 system, incorporated by reference herein.

As used herein, the term "congeal point" may refer to the temperature at which the wax sample being cooled develops a "set" or resistance to flow. At that temperature, the wax may be at or close to the solid state, or it may be semisolid, depending on the composition of the wax being tested. The congeal point may be measured using ASTM-D938, incorporated by reference herein.

As used herein, the term "needle penetration" may refer to the relative hardness of the wax sample. The needle penetration may be measured using ASTM-D1321-02a, incorporated by reference herein.

As used herein, the term "peak force" may refer to the relative hardness of the wax sample. In certain embodiments, the peak force measurement is used to measure the relative hardness of a blended wax sample comprising an amidated metathesized natural oil and a natural oil. The peak force may be measured using a texture analyzer such as TA XT Plus, manufactured by Stable Micro Systems. This particular instrument has a movable arm equipped with force sensors that is programmed to push a probe into the sample and record the resistance to penetration as the probe is pushed into the sample. A 45° conical stainless steel probe (TA15) may be pushed into the sample at a rate of 0.5 mm/sec to a depth of 10 mm below the surface of the sample. The peak (maximum) force recorded by the instrument may be taken as a measure of the hardness of the sample.

As used herein, the term "amine" refers to any compound carrying at least one amino group such as ammonia, a mono-substituted amine (having one non-hydrogen substituted group such as an alkyl, aryl, alkyl-amino, aryl-amino, ether amino, amino acid or ester, thiol amino, urea, or thiourea group), a di-substituted amine (having two non-hydrogen substituted groups), or an amino-alcohol, unless otherwise indicated.

As used herein, the term "amidated metathesized natural oil" refers to amide compositions formed from the reaction of an amine and a metathesized natural oil.

As used herein, the term "diacid functionality" may refer to the following structure formed from the metathesis reaction of a natural oil, —(C=O)—$X_1$—$X_2$—(C=O)—, wherein $X_1$ and $X_2$ are independently selected from the group consisting of $C_4$-$C_{28}$ saturated or unsaturated alkyl chains from either a fatty acid of a natural oil, or a derivative thereof formed by a metathesis reaction. In another embodiment, $X_1$ and $X_2$ are independently selected from the group consisting of $C_8$-$C_{28}$ saturated or unsaturated alkyl chains from either a fatty acid of a natural oil, or a derivative thereof formed by a metathesis reaction.

A number of valuable amide wax compositions may be prepared by reacting an amine with an ester-functional group of a metathesized natural oil in the presence of a basic catalyst or heat to form an amidated metathesized natural oil. This reaction may generate amidated metathesized natural oil compositions having unique properties over other forms of amide waxes, natural oils, or metathesized natural oils. Such unique properties may include a higher drop point, higher congeal point, leveling effect, improved hardness, improved malleability, improved emulsifiability, improved functionality, improved viscosity, and/or improved compatibility with other materials (such as triglyceride oils and waxes, polyamides, stearic acid, ethylene vinyl acetate copolymers, tackifier resins, and paraffins in low concentration). In certain embodiments, it is possible to tailor the range of certain properties (such as drop point or hardness) by modifying the amount or type of amine used in the reaction with the metathesized natural oil.

In certain embodiments, the amidated metathesized natural oil may possess properties equal to or improved over commercial waxes for various applications such as: high temperature lubricants, rheology modifiers, plastic processing applications (e.g., release agents, slip agents, anti-tack agents, nucleation and lubrication for plastics), polymer processing applications, wood/plastic composites, hot melt adhesives, slip agents for paraffin wax coatings, metal working applications, road construction waxes, emulsifying waxes, binders for cosmetics, softening point/hardness modifiers, thickening agents, metal powder (sintering) processing applications, wetting agents, foam stabilizers, polishes, coatings, structurants (i.e., the ability of the wax to partially or fully solidify a mixture of oils), pigment carriers, corrosion inhibitors, or inks/toners. In one embodiment, the amidated metathesized natural oil composition is used as a structurant or nucleating agent for a cosmetic application, adhesive application, or clarifying agent application. In another embodiment, the amidated metathesized natural oil composition is used as a thickener or pearlescent for a hair care or lotion application. In yet another embodiment, the amidated metathesized natural oil composition is used in a powder corrosion coating to achieve a leveling effect. In certain embodiments, the amidated metathesized natural oil composition is used in sunscreen, lip balm, lipstick, sunscreen stick, hair pomade, or hand/body moisturizing lotion.

In addition, the amidated metathesized natural oil formed from the amine-metathesized natural oil reaction may include certain advantages over commercial waxes such as simple, cost-effective production, reduced variability, improved sourcing, and biorenewability.

In certain embodiments, the natural oil in the amidated metathesized natural oil composition has been metathesized in the presence of a metathesis catalyst to form a metathesis oligomer (or "metathesized natural oil"). The metathesis catalyst in this reaction may include any catalyst or catalyst system that catalyzes a metathesis reaction. Any known metathesis catalyst may be used, alone or in combination with one or more additional catalysts. Non-limiting exemplary metathesis catalysts and process conditions are described in PCT/US2008/009635, pp. 18-47, incorporated by reference herein. A number of the metathesis catalysts as shown are manufactured by Materia, Inc. (Pasadena, Calif.).

Metathesis is a catalytic reaction that involves the interchange of alkylidene units among compounds containing one or more double bonds (i.e., olefinic compounds) via the formation and cleavage of the carbon-carbon double bonds. The metathesis reaction of the natural oil feedstock having unsaturated polyol esters results in the oligomerization of the unsaturated polyol ester having a mixture of olefins and esters that may comprise one or more of: metathesis monomers, metathesis dimers, metathesis trimers, metathesis tetramers, metathesis pentamers, and higher order metathesis oligomers (e.g., metathesis hexamers), as shown in FIG. 1. A metathesis dimer refers to a compound formed when two unsaturated polyol ester molecules are covalently bonded to one another by a metathesis reaction. In certain embodiments, the molecular weight of the metathesis dimer is greater than the molecular weight of the individual unsaturated polyol ester molecules from which the dimer is formed. A metathesis trimer refers to a compound formed when three unsaturated polyol ester molecules are covalently bonded together by metathesis reactions. A metathesis trimer may be formed by the cross-metathesis of a metathesis dimer with an unsaturated polyol ester. A metathesis tetramer refers to a compound formed when four unsaturated polyol ester molecules are covalently bonded together by metathesis reactions. A metathesis tetramer may be formed by the cross-metathesis of a metathesis trimer with an unsaturated polyol ester. Metathesis tetramers may also be formed, for example, by the cross-metathesis of two metathesis dimers. Higher order metathesis oligomers (such as metathesis pentamers and metathesis hexamers) may also be formed.

In certain embodiments, the metathesized natural oil in the amidated metathesized natural oil composition is derived from vegetable oil, algal oil, animal fat, tall oil, derivatives of these oils, or mixtures thereof. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, and castor oil. Representative non-limiting examples of animal fats include lard, tallow, poultry fat, yellow grease, and fish oil. Representative non-limiting examples of natural oil derivatives include metathesis oligomers, gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a natural oil feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

In some embodiments, the metathesized natural oil is a metathesized vegetable oil, metathesized algal oil, metathesized animal fat, metathesized tall oil, metathesized derivatives of these oils, and mixtures thereof. In one embodiment, the metathesized vegetable oil is metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, and mixtures thereof. In another embodiment, the metathesized natural oil is a metathesized animal fat, for example, metathesized lard, metathesized tallow, metathesized poultry fat, metathesized fish oil, metathesized derivatives of these oils, and mixtures thereof.

In certain embodiments, the metathesized natural oil in the amidated metathesized natural oil composition has been "hydrogenated" (i.e., full or partial hydrogenation of the unsaturated carbon-carbon bonds in the metathesized natural oil) in the presence of a hydrogenation catalyst to form a hydrogenated metathesized natural oil. In one embodiment, the metathesized natural oil is fully hydrogenated. In another embodiment, the natural oil is partially hydrogenated before it is subjected to the metathesis reaction. In another embodiment, the natural oil is metathesized prior to being subjected to partial or full hydrogenation. Any known or future-developed hydrogenation catalysts may be used, alone or in combination with one or more additional catalysts. Non-limiting exemplary hydrogenation catalysts and process conditions are described in PCT/US2007/000610 and PCT/US2008/009635, pp. 47-51, incorporated by reference herein.

Representative examples of hydrogenated metathesized natural oils include hydrogenated metathesized vegetable oil, hydrogenated metathesized algal oil, hydrogenated metathesized animal fat, hydrogenated metathesized tall oil, hydrogenated metathesized derivatives of these oils, and mixtures thereof. In one embodiment, the hydrogenated metathesized vegetable oil is hydrogenated metathesized canola oil, hydrogenated metathesized rapeseed oil, hydrogenated metathesized coconut oil, hydrogenated metathesized corn oil, hydrogenated metathesized cottonseed oil, hydrogenated metathesized olive oil, hydrogenated metathesized palm oil, hydrogenated metathesized peanut oil, hydrogenated metathesized safflower oil, hydrogenated metathesized sesame oil, hydrogenated metathesized soybean oil, hydrogenated metathesized sunflower oil, hydrogenated metathesized linseed oil, hydrogenated metathesized palm kernel oil, hydrogenated metathesized tung oil, hydrogenated metathesized jatropha oil, hydrogenated metathesized mustard oil, hydrogenated metathesized camelina oil, hydrogenated metathesized pennycress oil, hydrogenated metathesized castor oil, hydrogenated metathesized derivatives of these oils, and mixtures thereof. In another embodiment, the hydrogenated metathesized natural oil is a hydrogenated metathesized animal fat such as hydrogenated metathesized lard, hydrogenated metathesized tallow, hydrogenated metathesized poultry fat, hydrogenated metathesized fish oil, hydrogenated metathesized derivatives of these oils, and mixtures thereof. In certain embodiments, the representative examples of hydrogenated methathesized natural oil have been fully hydrogenated. In one embodiment, the natural oil is a hydrogenated metathesized soybean oil ("HMSBO"). In particular, S-55 is a hydrogenated metathesized soybean oil available from Elevance Renewable Sciences, Bolingbrook, Ill.

The amine compound(s) selected for the reaction with the metathesized natural oil may be ammonia or a compound containing one or more primary or secondary amino groups. In certain embodiments, the amine is a mono-substituted amine having one non-hydrogen substituted group (having one non-hydrogen substituted group such as an alkyl, aryl, alkyl-amino, aryl-amino, ether amino, amino acid or ester, thiol amino, urea, or thiourea group), a di-substituted amine having two non-hydrogen substituted groups, an amino-alcohol, or a combination thereof. In certain non-limiting embodiments, the amine is a mono-substituted or di-substituted amine such as: methylamine, dimethylamine, ethylamine, diethylamine, propylamine, dipropylamine, butylamine, dibutylamine, pentylamine, dipentylamine, hexylamine, dihexylamine, heptylamine, diheptylamine, octylamine, dioctylamine, or a mixture thereof. In other non-limiting embodiments, the amine is an amino-alcohol such as: methanolamine, dimethanolamine, ethanolamine, diethanolamine, propanolamine, dipropanolamine, butanolamine, dibutanolamine, pentanolamine, dipentanolamine, hexanolamine, dihexanolamine, heptanolamine, diheptanolamine, octanolamine, dioctanolamine, aniline, or a mixture thereof. In yet other non-limiting embodiments, the amine is a diamine such as: ethylenediamine (1,2-ethanediamine), 1,3-propanediamine, 1,4-butanediamine (putrescine), 1,5-pentanediamine, 1,6-hexanediamine, 1,7-heptanediamine, 1,8-octanediamine, 1,3-bis(aminomethyl) cyclohexane, meta-xylenediamine, 1,8-naphthalenediamine, p-phenylenediamine, N-(2-aminoethyl)-1,3-propanediamine, or a mixture thereof. In yet other non-limiting embodiments, the amine is a triamine or tetramine such as: diethylenetriamine, dipropylenetriamine, dibutylenetriamine, dipentylenetriamine, dihexylenetriamine, diheptylenetriamine, dioctylenetriamine, spermidine, melamine, triethylenetetramine, tripropylenetetramine, tributylenetetramine, tripentylenetetramine, trihexylenetetramine, triheptylenetetramine, trioctylenetetramine, hexamine, or a mixture thereof. In another embodiment, the amine is an imidazole or oxazolidine.

In certain embodiments, the amine is an amino acid or ester, urea, or a thiol amine. In other embodiments, the amine is an ether amine. In one particular embodiment, the amine is a polyether amine or polyoxyalkyleneamine having a backbone based on either propylene oxide, ethylene oxide or a mixture thereof. Commercial sources of ether amines include the JEFFAMINE® product family, from Huntsman Performance Products, The Woodlands, Tex., USA.

In one embodiment, the amine is selected from the group consisting of: ethanolamine, diethanolamine, diethylamine, ethylenediamine (1,2-ethanediamine), hexamethyleneamine, and mixtures thereof. In one embodiment, the amine is ethylenediamine. In another embodiment, the amine is diethanolamine.

In certain embodiments, the amine is a polar compound that is useful for forming a hydrous amidated metathesized natural oil composition. The hydrous composition is capable of being water dispersible and improving the viscosity of the wax composition. Non-limiting examples of polar amines include amino-alcohols such as: methanolamine, dimethanolamine, ethanolamine, diethanolamine, propanolamine, dipropanolamine, butanolamine, dibutanolamine, pentanolamine, dipentanolamine, hexanolamine, dihexanolamine, heptanolamine, diheptanolamine, octanolamine, dioctanolamine, aniline, or mixtures thereof.

In other embodiments, the amine is a non-polar compound that is useful for forming an anhydrous amidated metathesized natural oil composition. Such anhydrous compositions may be capable of improving the hardness and drop point of the wax composition.

In one embodiment, the amount of amine present in the amine-metathesized natural oil reaction is between approximately 0.1 percent by weight and 30 percent by weight of the metathesized natural oil present. In other embodiments, the amount of basic catalyst is between approximately 0.1 percent by weight and 10 percent by weight of the metathesized natural oil or between approximately 1 percent by weight and 15 percent by weight of the metathesized natural oil. Alternatively, the amount of amine added to the reaction can be expressed in terms of the ratio of amine equivalents in the amine to ester equivalents in the metathesized natural oil. In one embodiment, the ratio of amine equivalents to ester equivalents is between approximately 1:100 and approximately 10:1. In another embodiment, the ratio of amine equivalents to ester equivalents is between approximately 1:10 and approximately 5:1. In other embodiments, the ratio of amine equivalents to ester equivalents is approximately 1:3, approximately 2:3, approximately 1:2, or approximately 1:1.

The basic catalyst that may be used to improve the reaction rate of the amine-metathesized natural oil reaction is a basic compound generally known to a person of skill in the art. In certain embodiments, the basic catalyst is sodium carbonate, lithium carbonate, sodium methanolate, potassium hydroxide, sodium hydride, potassium butoxide, potassium carbonate, or a mixture thereof. In certain embodiments, the basic catalyst may be added to the reaction between the amine and metathesized natural oil in dry form or dissolved in water, alcohol, or another aprotic solvent suitable to the type of catalyst used.

In other embodiments, the reaction rate of the amine-metathesized natural oil reaction is improved by heating the amine-metathesized natural oil mixture (with or without a basic catalyst present) to at least 100° C., at least 120° C., at least 140° C., at least 160° C., or between approximately 100° C. and approximately 200° C.

In one embodiment, the amount of basic catalyst added to the reaction is between approximately 1 percent by weight and 10 percent by weight of the metathesized natural oil present. In other embodiments, the amount of basic catalyst is between approximately 0.1 percent by weight and 1.0 percent by weight of the metathesized natural oil or between approximately 0.01 percent by weight and 0.1 percent by weight of the metathesized natural oil. In another embodiment, the amount of basic catalyst is approximately 0.5 percent by weight of the metathesized natural oil.

In one embodiment, the amine-metathesized natural oil reaction is conducted in a nitrogen or other inert atmosphere. In certain embodiments, the reaction is conducted under atmospheric conditions and the reactor temperature is between approximately 80-250° C., between approximately 120-180° C., or between approximately 120-160° C. In certain embodiments, the reactor temperature is held for approximately 1-24 hours, approximately 4-24 hours, approximately 1 hour, approximately 2 hours, approximately 4 hours, or approximately 6 hours.

In certain embodiments, following the amine-metathesized natural oil reaction, the product mixture is vacuum pumped for at least 30 minutes or at least 1 hour to separate the water, any unreacted amine, and/or glycerol from the amidated metathesized natural oil product. In another embodiment, paraffin byproduct from the metathesis and hydrogenation reactions can be separated from the amidated metathesized natural oil product.

When the metathesized natural oil is reacted with at least one amine in the presence of the basic catalyst or heat, the ester functionality is replaced by an amide to form an amidated metathesized natural oil. When the amide is formed from an ester which has been linked by the metathesis reaction to another ester, a molecule of the following structure is formed:

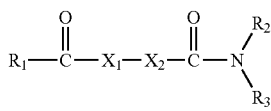

When the amide is formed from an ester which has not been linked to another ester, the following structure is formed:

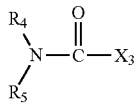

In these structures, $R_1$ is selected from the group consisting of:

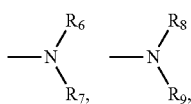 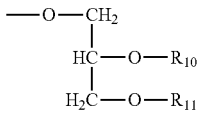

$R_2$, $R_3$, $R_4$, $R_5$, $R_6$, $R_7$, $R_8$, and $R_9$ are independently selected from the group consisting of hydrogen, alcohols, alkyls, aryls, alkyl-amines, aryl-amines, ether amines, amino acids and esters, thiol amines, ureas, and thioureas.

$R_{10}$ and $R_{11}$ are independently selected from the group consisting of:

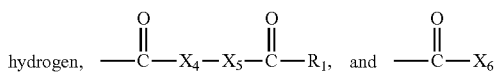

$X_1$, $X_2$, $X_3$, $X_4$, $X_5$, and $X_6$ are independently selected from the group consisting of $C_4$-$C_{28}$ saturated or unsaturated alkyl chains from either a fatty acid of a natural oil, or a derivative thereof formed by a metathesis reaction.

In other embodiments, $X_1$, $X_2$, $X_3$, $X_4$, $X_5$, and $X_6$ are independently selected from the group consisting of $C_8$-$C_{28}$ saturated or unsaturated alkyl chains from either a fatty acid of a natural oil, or a derivative thereof formed by a metathesis reaction.

In certain embodiments, $R_2$, $R_3$, $R_4$, $R_5$, $R_6$, $R_7$, $R_8$, and $R_9$ may form at least one amine selected from the group consisting of: methylamine, dimethylamine, ethylamine, diethylamine, propylamine, dipropylamine, butylamine, dibutylamine, pentylamine, dipentylamine, hexylamine, dihexylamine, heptylamine, diheptylamine, octylamine, dioctylamine, methanolamine, dimethanolamine, ethanolamine, diethanolamine, propanolamine, dipropanolamine, butanolamine, dibutanolamine, pentanolamine, dipentanolamine, hexanolamine, dihexanolamine, heptanolamine, diheptanolamine, octanolamine, dioctanolamine, aniline, ethylenediamine (1,2-ethanediamine), 1,3-propanediamine, 1,4-butanediamine (putrescine), 1,5-pentanediamine, 1,6-hexanediamine, 1,7-heptanediamine, 1,8-octanediamine, 1,3-bis(aminomethyl)cyclohexane, meta-xylenediamine, 1,8-naphthalenediamine, p-phenylenediamine, N-(2-aminoethyl)-1,3-propanediamine, diethylenetriamine, dipropylenetriamine, dibutylenetriamine, dipentylenetriamine, dihexylenetriamine, diheptylenetriamine, dioctylenetriamine, spermidine, melamine, triethylenetetramine, tripropylenetetramine, tributylenetetramine, tripentylenetetramine, trihexylenetetramine, triheptylenetetramine, trioctylenetetramine, hexamine, imidazole, oxazolidine, or mixtures thereof. In another embodiment, $R_2$, $R_3$, $R_4$, $R_5$, $R_6$, $R_7$, $R_8$, and $R_9$ may form at least one amine selected from the group consisting of: amino acids or esters, ureas, thiol amines, ether amines, or mixtures thereof.

In one embodiment, the amidated metathesized natural oil comprises a "diacid functionality" [e.g., —(C═O)—$X_1$—$X_2$—(C═O)—]. In another embodiment, the amidated metathesized natural oil contains the diacid functionality and a glycerol backbone of the metathesized natural oil.

In certain embodiments, in addition to the amidated metathesized natural oil product, the reaction between the metathesized natural oil and amine produces a hydroxymetathesis oligomer co-product having the following structure:

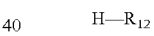

wherein $R_{12}$ is:

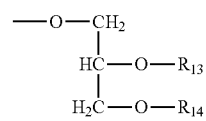

In these structures, $R_{13}$ and $R_{14}$ are independently selected from the group consisting of:

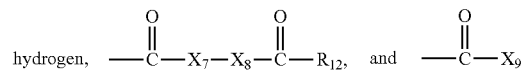

$X_7$, $X_8$, and $X_9$ are independently selected from the group consisting of $C_4$-$C_{28}$ saturated or unsaturated alkyl chains from either a fatty acid of a natural oil, or a derivative thereof formed by a metathesis reaction.

In other embodiments, $X_7$, $X_8$, and $X_9$ are independently selected from the group consisting of $C_8$-$C_{28}$ saturated or unsaturated alkyl chains from either a fatty acid of a natural oil, or a derivative thereof formed by a metathesis reaction.

In one particular example, the reaction of an amine (in this case, ethylenediamine) and a natural oil metathesis dimer (shown below) may form a variety of products based on the location of the amidation reaction(s). In the case of the metathesis dimer below, the amidation reaction(s) may occur at one or more of the six labeled ester locations (shown below).

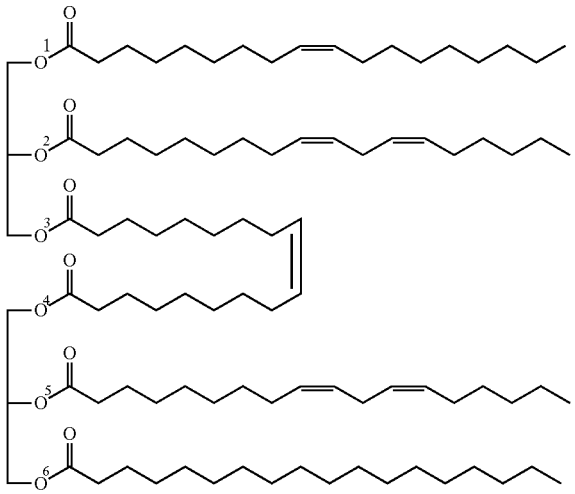 [SMILES: CCCCC/C=C\C/C=C\CCCCCCCC(=O)OC(COC(=O)CCCCCCC/C=C\CCCCCCCC)COC(=O)CCCCCCC/C=C\CCCCCCCC(=O)OCC(COC(=O)CCCCCCCCCCCCCCCCC)OC(=O)CCCCCCC/C=C\C/C=C\CCCCC]

Should the amidation reaction between the metathesis dimer and ethylenediamine occur at ester location 1, the amide product formed from the reaction would include:

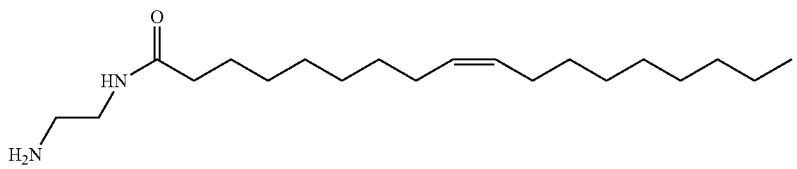 [SMILES: CCCCCCCC/C=C\CCCCCCCC(=O)NCCN]

and a hydroxy-metathesis oligomer co-product:

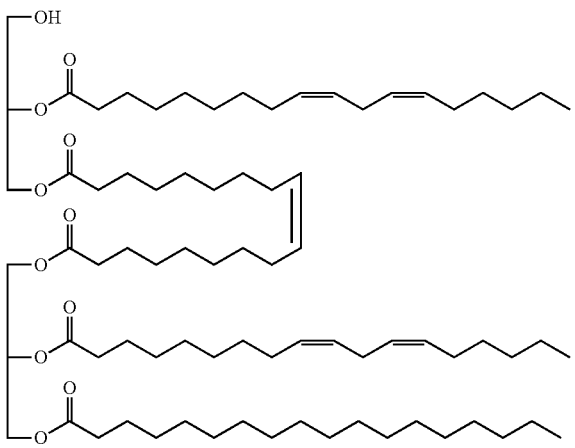 [SMILES: CCCCC/C=C\C/C=C\CCCCCCCC(=O)OC(CO)COC(=O)CCCCCCC/C=C\CCCCCCCC(=O)OCC(COC(=O)CCCCCCCCCCCCCCCCC)OC(=O)CCCCCCC/C=C\C/C=C\CCCCC]

Amidation reactions at ester locations 2, 5, and 6 would produce similar amide products and hydroxy-metathesis oligomer co-products.

Should the amidation reaction between the metathesis dimer and ethylenediamine occur at ester location 3, the amide product formed from the reaction would include:

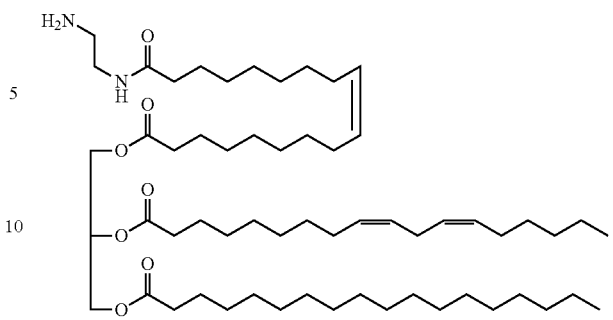

and a hydroxy-metathesis oligomer co-product:

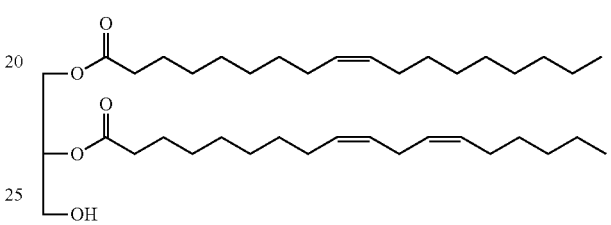

An amidation reaction at ester location 4 would produce a similar product and hydroxy-metathesis oligomer co-product.

In some embodiments, the amidation reaction may occur at multiple ester locations of the metathesized natural oil. For example, should the amidation reaction occur at ester locations 3 and 4 of the metathesis dimer (shown above) with ethylenediamine, the amide product formed from the reaction would include:

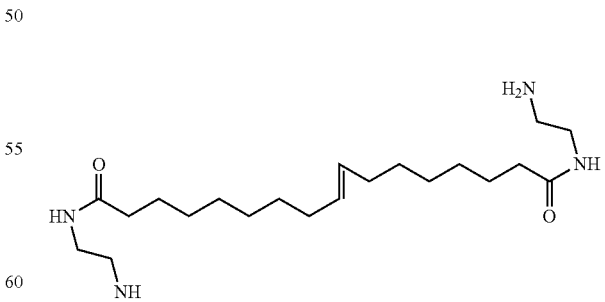

Should the amidation reaction occur at ester locations 3 and 6, the amide products formed from the reaction would include:

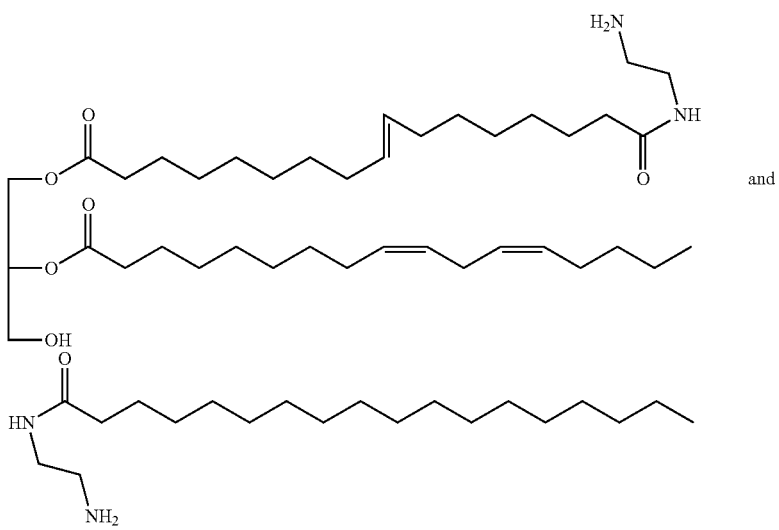

In some embodiments, the amine may replace more than one ester functionality of the metathesized natural oil. In such embodiments, di- or tri-substitution of the amino group typically requires more severe reaction conditions than the first substitution reaction. The reaction of an amine (in this non-limiting example, ethylenediamine) and a natural oil metathesis dimer (shown above) may form an amide with multiple ester-functionality substitutions, such as the following examples:

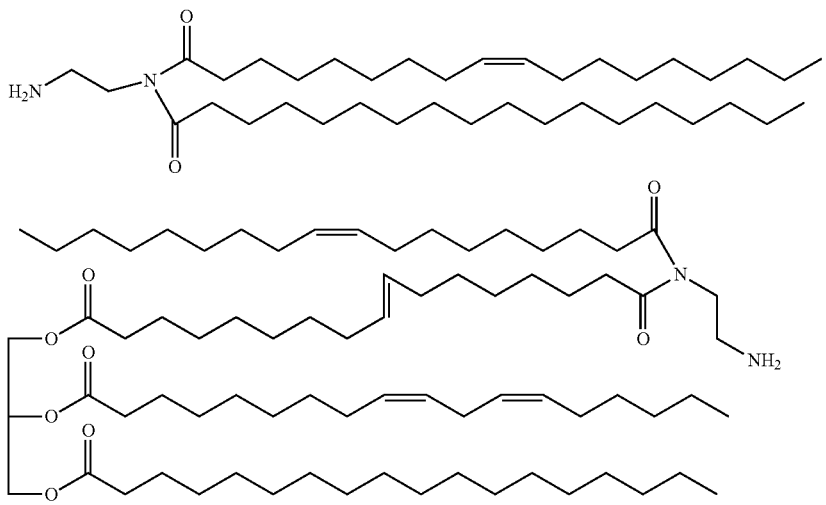

In other embodiments, when the metathesized natural oil is reacted with an amine having more than one amino group (i.e., "multi-amine") in the presence of a basic catalyst, a cross-linked amidated metathesized natural oil may be produced where more than one amino group reacts with an ester functionality to form the cross-linked amidated metathesized natural oil. The reaction mechanism is shown below in (III), using ethylenediamine as a non-limiting example:

$$2R^1(C=O)OR^2 + NH_2CH_2CH_2NH_2 \rightarrow R^1(C=O)NHCH_2CH_2NH(C=O)R^1 + 2R^2OH \quad (III)$$

wherein $R^1$ may be a fatty acid ester or metathesized fatty acid ester of the natural oil and $R^2$ includes the glycerol backbone of the natural oil, $CH_2CH(OR)CH_2(OR')$, where R and R' may be a fatty acid esters or metathesized fatty acid esters of the natural oil.

For example, the reaction of a multi-amine (in this case, ethylenediamine) and a natural oil metathesis dimer (shown below) may form a variety of cross-linked products based on the location of the amidation reaction(s). For example, should the react with ester group 1 and ester group 6 (of the same or different compound), the cross-linked product would include:

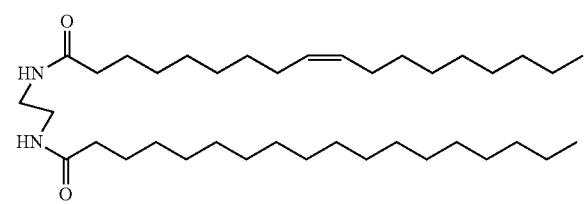 [SMILES: CCCCCCCC/C=C\CCCCCCCC(=O)NCCNC(=O)CCCCCCCCCCCCCCCCC]

Should the multi-amine react with ester group 1 and ester group 3 (of the same or different compound), the cross-linked product would include:

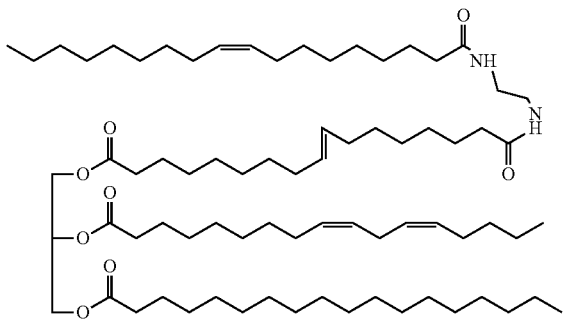 [SMILES: CCCC/C=C\C/C=C\CCCCCCCC(=O)OC(COC(=O)CCCCCCC/C=C/CCCCCCC(=O)NCCNC(=O)CCCCCCC/C=C\CCCCCCCC)COC(=O)CCCCCCCCCCCCCCCCC]

Figure 2:
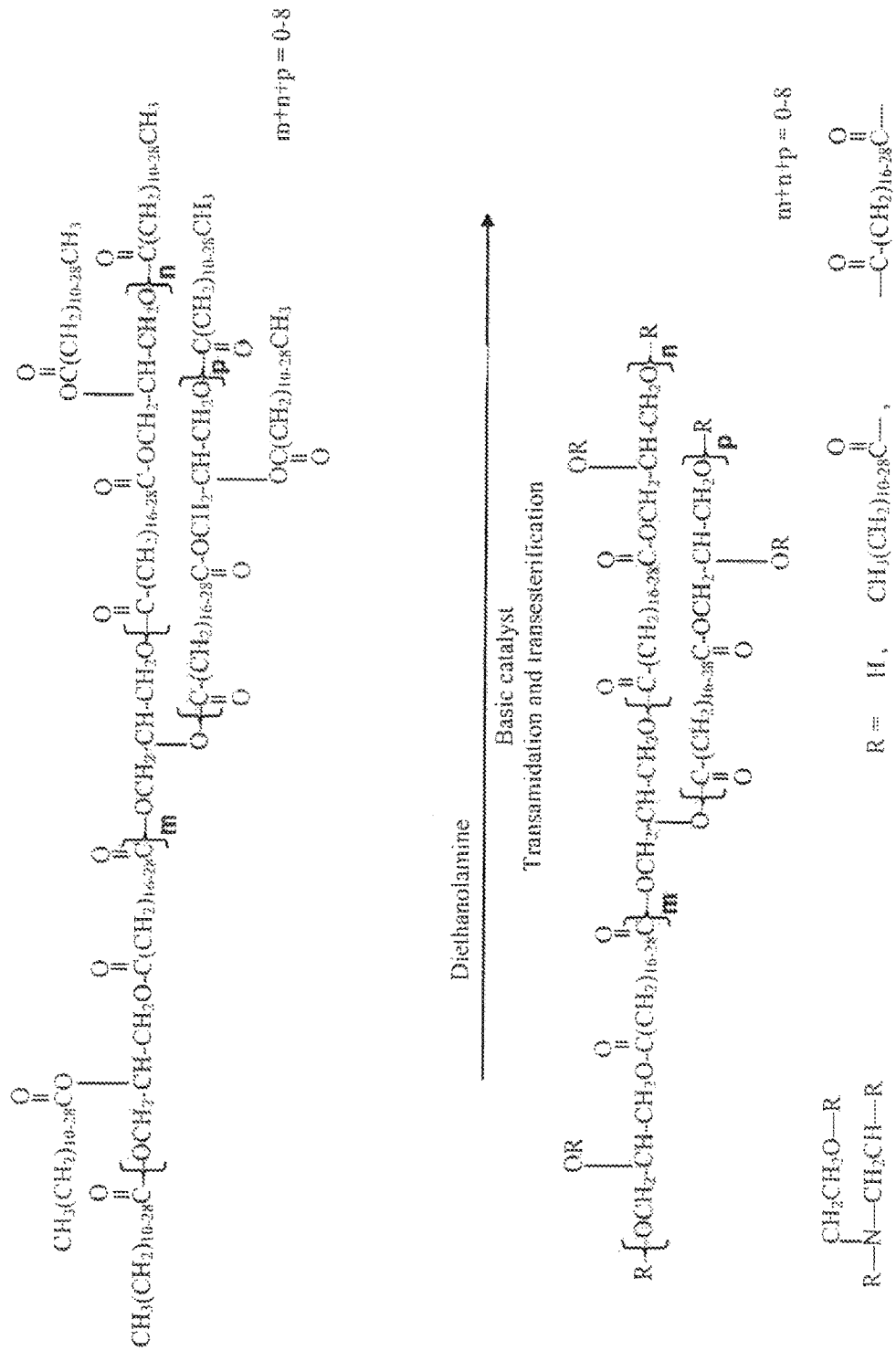
FIG. 2 depicts an exemplary reaction scheme between a hydrogenated metathesized natural oil and an amine.

In one embodiment, as shown in FIG. 2, hydrogenated metathesized soybean oil (HMSBO) is reacted with diethanolamine in the presence of a basic catalyst to produce an amidated metathesized natural oil composition comprising fatty acid amides, mixed amide-esters, fatty acid salts, triglycerides, diglycerides, monoglycerides, natural oil oligomers, paraffins, and/or free glycerol.

Figure 3:
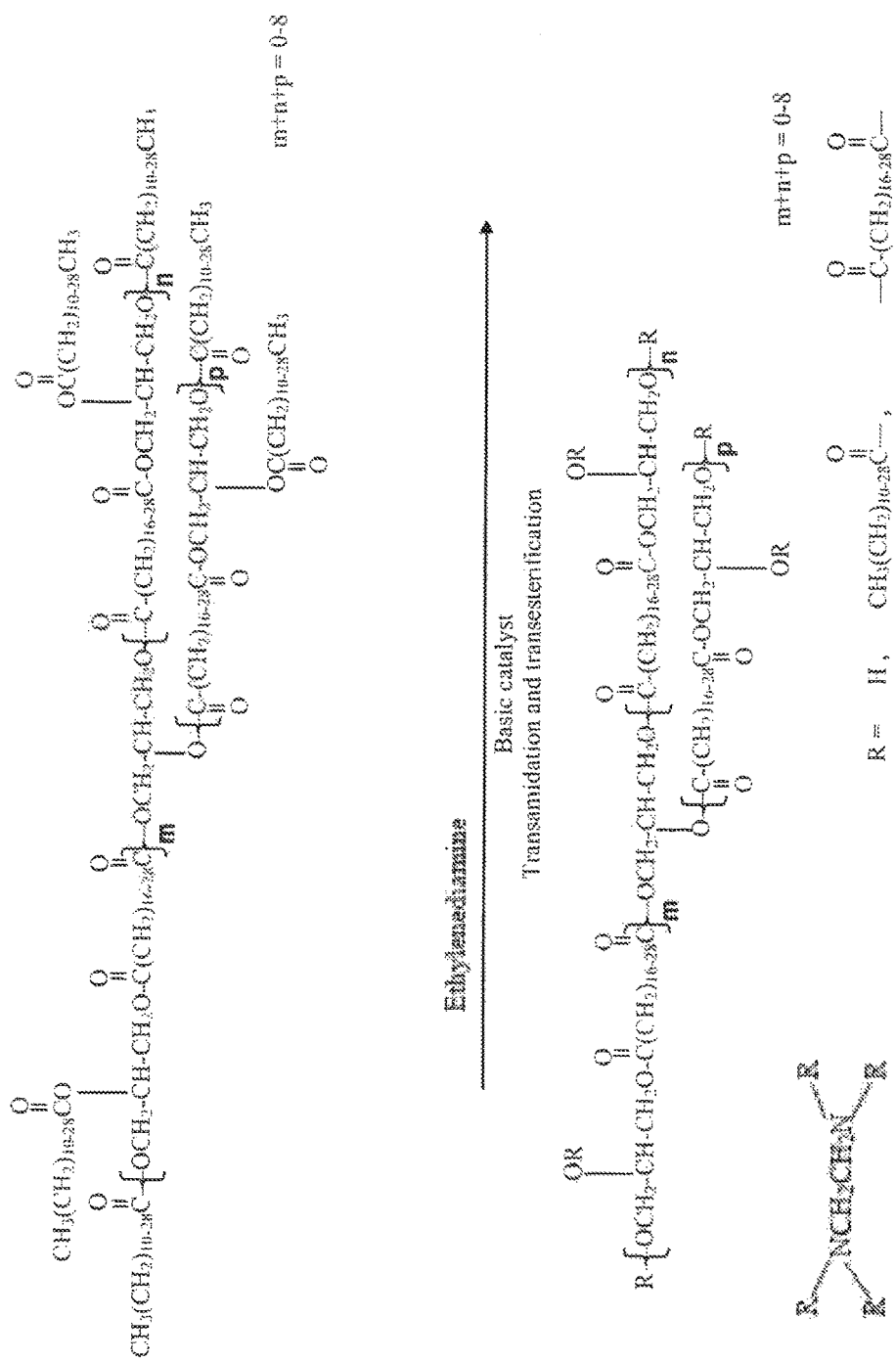
FIG. 3 depicts an exemplary reaction scheme between a hydrogenated metathesized natural oil and an amine.

In another embodiment, as shown in FIG. 3, hydrogenated metathesized soybean oil (HMSBO) is reacted with ethylenediamine in the presence of a basic catalyst to produce an amidated metathesized natural oil composition comprising fatty acid amides, mixed amide-esters, fatty acid salts, triglycerides, diglycerides, monoglycerides, natural oil oligomers, paraffins, and/or free glycerol.

It is noted that when the metathesized natural oil comprises paraffinic compounds, such as those found in various hydrogenated metathesized natural oils, the paraffinic compounds do not react with the amine and exit the reaction unaltered. In certain embodiments, depending on the potential use of the amidated metathesized natural oil product formed in the reaction, the paraffinic compounds may be partially or fully separated from the amide components.

In addition, the basic catalyst may react with the triglycerides and oligomers thereof to hydrolyze the ester groups and form the corresponding fatty acid salts. The reaction mechanisms are shown below in (IV):

$$R^1(C{=}O)OR^2+CH_3ONa+H_2O \rightarrow R^1(C{=}O)ONa+$$
$$R^2OH+CH_3OH\uparrow 2R^1(C{=}O)OR^2+Na_2CO_3+$$
$$H_2O \rightarrow 2R^1(C{=}O)ONa+2R^2OH+CO_2\uparrow R^1$$
$$(C{=}O)OR^2+KOH \rightarrow R^1(C{=}O)OK+R^2OH \qquad (IV)$$

wherein $R^1$ and $R^2$ are defined above in equation (III).

In certain embodiments, the product composition from the amine-metathesized natural oil reaction may comprise fatty acid amides (including polyamides), mixed amide-esters, fatty acid salts, triglycerides, diglycerides, monoglycerides, natural oil oligomers, olefins, paraffins, and/or free glycerol.

In one embodiment, the product composition from the amine-metathesized natural oil reaction is subjected to partial or full hydrogenation (in the instance where the natural oil was partially to fully hydrogenated prior to the amine-metathesized natural oil reaction). As previously noted, any known or future-developed hydrogenation catalysts may be used, alone or in combination with one or more additional catalysts. Non-limiting exemplary hydrogenation catalysts and process conditions are described in PCT/US2007/000610 and PCT/US2008/009635, pp. 47-51, incorporated by reference herein.

In some embodiments, the product composition from the amine-methathesized natural oil reaction is epoxidized via any suitable peroxyacid (or peracid). Peroxyacids are acyl hydroperoxides and are most commonly produced by the acid-catalyzed esterification of hydrogen peroxide. Examples of hydroperoxides that may be used include, but are not limited to, hydrogen peroxide, tert-butylhydroperoxide, triphenylsilyhydroperoxide, cumylhydroperoxide, and mixtures thereof. In one particular embodiment, the hydroperoxide is hydrogen peroxide.

In certain embodiments, the amine-metathesized natural oil reaction produces a product composition comprising approximately: 4-99 percent by weight fatty acid amides (including monoamides and polyamides) and mixed amide-esters; 1-2 percent by weight fatty acid salts; 0-95 percent by weight triglycerides, diglycerides, monoglycerides, natural oil oligomers; 0-15 percent by weight paraffins; and 0-9 percent by weight free glycerol.

In other embodiments, the amine-metathesized natural oil reaction produces a product composition comprising approximately: 4-40 mol % fatty acid amides (including monoamides and polyamides) and mixed amide-esters; 0.1-2 mol % fatty acid salts; 0.3-88 mol % triglycerides, diglycerides, monoglycerides, natural oil oligomers; 7-12 mol % paraffins; and 0.5-4 mol % free glycerol.

In another embodiment, the amine-metathesized natural oil reaction produces a product composition comprising approximately: 10-20 mol % fatty acid amides (including monoamides and polyamides) and mixed amide-esters; 0.1-2 mol % fatty acid salts; 60-85 mol % triglycerides, diglycerides, monoglycerides, natural oil oligomers; 3-10 mol % paraffins; and 1-6 mol % free glycerol. The composition can be described with greater delineation of the chemical species resulting from a reaction with ethylenediamine as comprising approximately: 10-15 mol % fatty acid diamides; 2-4 mol % diamides of metathesis oligomers; 0.5-2 mol % diamides of hydroxy-metathesis oligomers; 40-60 mol % metathesis oligomers; and 15-25 mol % hydroxy-metathesis oligomers.

In one particular embodiment, the amine-metathesized natural oil reaction produces a product composition comprising approximately: 16 mol % fatty acid amides (including monoamides and polyamides) and mixed amide-esters; 0.1-2 mol % fatty acid salts; 74 mol % triglycerides, diglycerides, monoglycerides, natural oil oligomers; 8 mol % paraffins; and 3 mol % free glycerol. The composition can be described with greater delineation of the chemical species resulting from a reaction with ethylenediamine as comprising approximately: 12 mol % fatty acid diamides; 3 mol % diamides of metathesis oligomers; 1 mol % diamides of hydroxy metathesis oligomers; 52 mol % metathesis oligomers; and 22 mol % hydroxy metathesis oligomers.

In certain embodiments, the amidated metathesized natural oil composition comprises various physical properties such as: (1) a light yellow to ocher color, (2) a glossy texture, (3) low melt viscosity (i.e., resistance to flow at certain temperatures), (4) good slip properties (coefficient of friction), (5) good non-stick properties, and/or (6) good miscibility with hydrogenated metathesized natural oils.

Because the metathesized natural oil comprises diacid characteristics [e.g., $(C{=}O)(CH_2)_{16\text{-}28}(C{=}O)$], the amidated metathesized natural oil composition produced by the amine-metathesized natural oil reaction comprises poly-functional material. Such poly-functional, diacid material offers the ability to control the drop point, congeal point, needle penetration, peak force, viscosity, slip/friction, etc. In certain embodiments, the characteristics of the amidated metathesized natural oil differ from typical fatty acid amides having no poly-functional, diacid properties.

In certain embodiments, the amidated metathesized natural oil comprises an increased drop point in comparison the metathesized natural oil composition. In certain embodiments, the drop point of the amidated metathesized natural oil increased by at least 10° C., at least 20° C., at least 30° C., at least 40° C., or at least 50° C. over a wax composition similar in all respects except that the metathesized natural oil is not amidated.

In one embodiment, the drop point of the amidated metathesized natural oil is between approximately 70° C. and approximately 200° C., between approximately 90° C. and approximately 190° C., greater than approximately 75° C., greater than approximately 95° C., or greater than approximately 150° C. In another embodiment, the drop point of the amidated metathesized natural oil is between approximately 70° C. and approximately 200° C., between approximately 80° C. and approximately 140° C., greater than approximately 80° C., or greater than approximately 130° C. In yet another embodiment, the drop point of the amide wax produced by the reaction of an amine and fatty acid methyl ester is between approximately 30° C. and approximately 150° C., between approximately 40° C. and approximately 140° C., greater than approximately 40° C., or greater than approximately 100° C.

In certain embodiments, the amidated metathesized natural oil comprises an increased congeal point in comparison the metathesized natural oil composition. In certain embodiments, the congeal point of the amide wax increased by at least 10° C., at least 20° C., at least 30° C., at least 40° C., or at least 50° C. over a wax composition similar in all respects except that the metathesized natural oil is not amidated.

In one embodiment, the congeal point of the amidated metathesized natural oil is between approximately 70° C. and approximately 150° C., between approximately 80° C. and approximately 140° C., greater than approximately 80° C., greater than approximately 90° C., or greater than approximately 130° C. In another embodiment, the congeal point of the amidated metathesized natural oil is between approximately 70° C. and approximately 200° C., between approximately 80° C. and approximately 140° C., greater than approximately 80° C., or greater than approximately 130° C. In yet another embodiment, the congeal point of the amide wax produced by the reaction of an amine and fatty acid methyl ester is between approximately 30° C. and approximately 150° C., between approximately 40° C. and approximately 140° C., greater than approximately 40° C., or greater than approximately 100° C.

In certain embodiments, the amidated metathesized natural oil comprises an increased hardness, as measured by needle penetration or peak force, in comparison the metathesized natural oil composition. In certain embodiments, the amidated metathesized natural oil was harder (as measured by needle penetration) by at least 1 dmm (decimillimeter), at least 2 dmm, at least 5 dmm, or at least 10 dmm over a wax composition similar in all respects except that the metathesized natural oil is not amidated. In certain embodiments, the amidated metathesized natural oil was harder by at least 0.1 kg, at least 0.2 kg, at least 0.4 kg, at least 0.6 kg, or at least 1 kg over a wax composition similar in all respects except that the metathesized natural oil is not amidated.

In certain embodiments, the amidated metathesized natural oil comprises a hardness, as measured by needle penetration, between approximately 1 dmm and approximately 40 dmm, or between approximately 4 dmm and approximately 19 dmm. In certain embodiments, the amidated metathesized natural oil comprises a hardness, as measured by peak force, between approximately 0.1 kg and approximately 2 kg, or between approximately 0.3 kg and approximately 1.5 kg.

In certain embodiments, the amidated metathesized natural oil can be blended with another natural oil wax composition. This may be done to improve or tailor the properties of the natural oil wax composition to have a certain drop point, congeal point, hardness (needle penetration or peak force), or other characteristic such as color, texture, viscosity, slip property, and/or non-stick property. In one embodiment, the amidated metathesized natural oil is hydrous and is blended with a water-based natural oil wax composition to form a water-based product such as sunscreen or hand/body lotion. In another embodiment, the amidated metathesized natural oil is anhydrous and is blended with a non-water based natural oil wax composition to form a product such as a lip balm, hair pomade, sunscreen stick, or lipstick. In certain embodiments, between approximately 0.01 percent by weight and approximately 20 percent by weight amidated metathesized natural oil is blended with the natural oil wax composition. In one embodiment, between approximately 0.01 percent by weight and 5 percent by weight of a hydrous amidated metathesized natural oil is blended with a water-based natural oil wax composition. In another embodiment, between approximately 5 percent by weight and 15 percent by weight of an anhydrous amidated metathesized natural oil is blended with a non-water based natural oil wax composition.

When dispersed into cosmetic oils, an amidated metathesized natural oil may provide a structuring effect. Structuring in this context refers the ability of a wax to partially or fully solidify a mixture of oils. Structurants are used to make products such as lipsticks or antiperspirant sticks. They are also used to thicken certain types for emulsion formulations, particularly water-in-oil emulsions where the continuous phase of the emulsion is composed of various cosmetic oils. The structuring effect may be evaluated by testing the viscosity of the emulsion. In certain embodiments, the formulation including the amidated metathesized natural oil has a viscosity between 13 centipoise (cP) and 33,000 cP, between 400 cP and 3000 cP, between 1000 cP and 2500 cP, or between 10,000 cP and 30,000 cP.

In certain embodiments, the amidated metathesized natural oil is blended with a natural oil or natural oil derivative composition (such as a fatty acid) to modify the hardness of the natural oil composition. In certain embodiments, the hardness of the natural oil composition is increased by at least 25%, 50%, 100%, or 200% by the addition of approximately 0.01 percent by weight, 0.1 percent by weight, 0.5 percent by weight, 1 percent by weight, 2 percent by weight, 5 percent by weight, 10 percent by weight, 20 percent by weight, 40 percent by weight, 60 percent by weight, or 80 percent by weight of the amidated metathesized natural oil to the natural oil composition. In one embodiment, the hardness of the natural oil composition is increased by at least 25% by the addition of less than approximately 20 percent by weight amidated metathesized natural oil to the natural oil composition. In another embodiment, the hardness of the natural oil composition is increased by at least 100% by the addition of less than approximately 20 percent by weight amidated metathesized natural oil to the natural oil composition.

In certain embodiments, the amidated metathesized natural oil is blended with a natural oil or natural oil derivative composition to increase the drop point of the natural oil composition. In certain embodiments, the drop point of the natural oil composition is increased by at least 5° C., 10° C., 20° C., 30° C., 40° C., or 50° C. by the addition of approximately 0.01 percent by weight, 0.1 percent by weight, 0.5 percent by weight, 1 percent by weight, 2 percent by weight, 5 percent by weight, 10 percent by weight, or 20 percent by weight amidated metathesized natural oil to the natural oil composition. In one embodiment, the drop point of the natural oil composition is increased by at least 5° C. by the addition of less than approximately 1 percent by weight amidated metathesized natural oil to the natural oil composition. In another embodiment, the drop point of the natural oil composition is increased by at least 50° C. by the addition of less than approximately 10 percent by weight amidated metathesized natural oil to the natural oil composition.

In other embodiments, the drop point of the amidated metathesized natural oil-natural oil blend is greater than the drop point of an amide wax derived from a fatty acid and amine reaction. In some embodiments, the amide wax-natural oil blend comprises approximately 0.01 percent by weight, 0.1 percent by weight, 0.5 percent by weight, 1 percent by weight, 2 percent by weight, 5 percent by weight, 10 percent by weight, or 20 percent by weight amide wax in the blend, and has a drop point that is at least 5° C., 10° C., 20° C., 30° C., 40° C., or 50° C. greater than the drop point of the amide wax derived from a fatty acid-amine reaction (e.g., ethylene bis stearamide formed from stearic acid and ethylenediamine).

In certain embodiments, the amidated metathesized natural oil is blended with a natural oil or natural oil derivative composition to increase the congeal point of the natural oil composition. Increasing the congeal point of the natural oil composition may be beneficial for various commercial embodiments such as hot melt adhesives. In one embodiment, the congeal point of the natural oil composition is increased by at least 5° C., 10° C., 20° C., 30° C., 40° C., or 50° C. by the addition of approximately 0.01 percent by weight, 0.1 percent by weight, 0.5 percent by weight, 1 percent by weight, 2 percent by weight, 5 percent by weight, 10 percent by weight, or 20 percent by weight amidated metathesized natural oil to the natural oil composition. In one embodiment, the congeal point of the natural oil composition is increased by at least 5° C. by the addition of less than approximately 0.5 percent by weight amidated metathesized natural oil to the natural oil composition. In another embodiment, the congeal point of the natural oil composition is increased by at least 50° C. by the addition of less than approximately 5 percent by weight amidated metathesized natural oil to the natural oil composition.

In other embodiments, the congeal point of the amidated metathesized natural oil-natural oil blend is greater than the congeal point of an amide wax derived from a fatty acid and amine reaction. In some embodiments, the amidated metathesized natural oil-natural oil blend comprises approximately 0.01 percent by weight, 0.1 percent by weight, 0.5 percent by weight, 1 percent by weight, 2 percent by weight, 5 percent by weight, 10 percent by weight, or 20 percent by weight amidated metathesized natural oil in the blend, and has a congeal point that is at least 5° C., 10° C., 20° C., 30° C., 40° C., or 50° C. greater than the congeal point of the amide wax derived from a fatty acid-amine reaction.

While the invention as described may have modifications and alternative forms, various embodiments thereof have been described in detail. It should be understood, however, that the description herein of these various embodiments is not intended to limit the invention, but on the contrary, the intention is to cover all modifications, equivalents, and alternatives falling within the spirit and scope of the invention as defined by the claims. Further, while the invention will also be described with reference to the following non-limiting examples, it will be understood, of course, that the invention is not limited thereto since modifications may be made by those skilled in the art, particularly in light of the foregoing teachings.

EXAMPLES

Example 1

70 grams of hydrogenated metathesized soybean oil (HMSBO) were melted and filled into a reactor under nitrogen gas. Next, 7.17 grams of ethylenediamine (i.e., a 2:3 ratio of amine equivalents in the amine to ester equivalents in the metathesized natural oil) were added under nitrogen at approximately 60° C. The mixture was stirred/homogenized for a few minutes and 0.35 grams of lithium carbonate basic catalyst were added (i.e., 0.5 percent by weight catalyst per HMSBO). The mixture was stirred and heated to 120-180° C. under nitrogen and held at 120-180° C. for several hours. After the reaction, the mixture was vacuum pumped for 30-60 minutes to drive off the water, unreacted amine, and glycerol. Finally, the resulting wax was decanted out of the flask and tested for physical properties such as drop point, congeal point, and needle penetration (shown below in Table 1A).

Example 2

70 grams of hydrogenated metathesized soybean oil (HMSBO) were melted and filled into a reactor under nitrogen gas. Next, 14.6 grams of ethanolamine (i.e., a 1:3 ratio of amine equivalents in the amine to ester equivalents in the metathesized natural oil) were added under nitrogen at approximately 60° C. The mixture was stirred/homogenized for a few minutes and 0.35 grams of lithium carbonate basic catalyst were added (i.e., 0.5 percent by weight catalyst per HMSBO). The mixture was stirred and heated to 120-180° C. under nitrogen and held at 120-180° C. for several hours. After the reaction, the mixture was vacuum pumped for 30-60 minutes to drive off the water, unreacted amine, and glycerol. Finally, the resulting wax was decanted out of the flask and tested for physical properties such as drop point, congeal point, and needle penetration (shown below in Table 1A).

Example 3

70 grams of hydrogenated metathesized soybean oil (HMSBO) were melted and filled into a reactor under nitrogen gas. Next, 17.4 grams of diethylamine (i.e., a 1:3 ratio of amine equivalents in the amine to ester equivalents in the metathesized natural oil) were added under nitrogen at approximately 60° C. The mixture was stirred/homogenized for a few minutes and 0.35 grams of lithium carbonate basic catalyst were added (i.e., 0.5 percent by weight catalyst per HMSBO). The mixture was stirred and heated to 120-180° C. under nitrogen and held at 120-180° C. for several hours. After the reaction, the mixture was vacuum pumped for 30-60 minutes to drive off the water, unreacted amine, and glycerol. Finally, the resulting wax was decanted out of the flask and tested for physical properties such as drop point, congeal point, and needle penetration (shown below in Table 1A).

Example 4

70 grams of hydrogenated metathesized soybean oil (HMSBO) were melted and filled into a reactor under nitrogen gas. Next, 13.9 grams of hexamethylenediamine (i.e., a 2:3 ratio of amine equivalents in the amine to ester equivalents in the metathesized natural oil) were added under nitrogen at approximately 60° C. The mixture was stirred/homogenized for a few minutes and 0.35 grams of lithium carbonate basic catalyst were added (i.e., 0.5 percent by weight catalyst per HMSBO). The mixture was stirred and heated to 120-180° C. under nitrogen and held at 120-180° C. for several hours. After the reaction, the mixture was vacuum pumped for 30-60 minutes to drive off the water, unreacted amine, and glycerol. Finally, the resulting wax was decanted out of the flask and tested for physical properties such as drop point, congeal point, and needle penetration (shown below in Table 1A).

Comparative Example 1

In this example, 70 grams of S-155 were melted and filled into a reactor under nitrogen gas. S-155 is a hydrogenated soybean oil sold by Elevance Renewable Sciences, Bolingbrook, Ill. Next, 7.17 grams of ethylenediamine (i.e., a 2:3 ratio of amine equivalents in the amine to ester equivalents in the metathesized natural oil) were added under nitrogen at approximately 60° C. The mixture was stirred/homogenized for a few minutes and 0.35 grams of lithium carbonate basic catalyst were added (i.e., 0.5 percent by weight catalyst per S-155). The mixture was stirred and heated to 120-180° C. under nitrogen and held at 120-180° C. for several hours. After the reaction, the mixture was vacuum pumped for 30-60 minutes to drive off the water, unreacted amine, and glycerol. Finally, the resulting wax was decanted out of the flask and tested for physical properties such as drop point, congeal point, and needle penetration (shown below in Table 1B).

TABLE 1A

Amide waxes produced by HMSBO amidation

| Example | Amine | Drop Point (° C.) | Congeal Point (° C.) | Needle Penetration (dmm) |
|---|---|---|---|---|
| 1 | Ethylenediamine | 163.0 | — | 4 |
| 2 | Ethanolamine | 100.7 | 90.5 | 19 |
| 3 | Diethylamine | 186.4 | 84.5 | 18 |
| 4 | Hexamethylene-diamine | 151.8 | 138 | — |

TABLE 1B

Amide waxes produced by S-155 (non-metathesized HSBO) amidation

| Comp. Example | Amine | Drop Point (° C.) | Congeal Point (° C.) | Needle Penetration (dmm) |
|---|---|---|---|---|
| 1 | Ethylenediamine | 105.8 | — | 3.6 |

Tables 1A and 1B show the results for drop point using the Mettler Drop Point FP80 system, congeal point using ASTM-D938, and needle penetration using ASTM-D1321-02a.

The majority of the HMSBO waxes in Table 1A had drop points greater than 150° C. (300° F.) with the exception of the amidated metathesized natural oil produced from ethanolamine. Ethanolamine forms esters in competition with amides. The ethylenediamine reaction produced the lowest needle penetration value (i.e., the hardest wax, similar to carnauba wax), which may be attributed to its diamide structure where both amine groups are close to each other (amide groups show strong interactions like the ones in structural proteins). The HMSBO reaction with ethanolamine and diethylamine produced waxes having hardness (19 dmm, 18 dmm) similar to beeswax. The highest drop point was observed with the diethylamine reaction caused by high viscosity.

In comparison, the amidation of non-metathesized soybean oil (S-155) had a drop point around 106° C., as shown in Table 1B.

Amidation of hydrogenated metathesized natural oils such as HMSBO appears to be an optimal route to achieve high melting point waxes that are improvements over the metathesized natural oil itself or a typical fatty acid amide having no poly-functional properties. Starting from the hydrogenated metathesized natural oil, the amidated metathesized natural oil product can be obtained in a one-pot reaction. Additionally, there is little to no waste or byproduct besides the replaced free glycerol (which can be removed to achieve increased drop point temperatures and increased hardness). Additional reduction of the paraffin content improves the hardness of the material due to the plasticizing effect of the paraffin.

Example 5

70 grams of fatty acid methyl ester derived from hydrogenated metathesized soybean oil were melted and filled into a reactor under nitrogen gas. Next, 7.17 grams of ethylenediamine (i.e., a 2:3 ratio of amine equivalents in the amine to ester equivalents in the FAME) were added under nitrogen at approximately 60° C. The mixture was stirred/homogenized for a few minutes and 0.35 grams of lithium carbonate basic catalyst were added (i.e., 0.5 percent by weight catalyst per FAME). The mixture was stirred and heated to 120-180° C. under nitrogen and held at 120-180° C. for several hours. After the reaction, the mixture was vacuum pumped for 30-60 minutes to drive off the water and unreacted amine. Finally, the resulting wax was decanted out of the flask and tested for physical properties such as drop point, congeal point, and needle penetration (shown below in Table 2).

Example 6

70 grams of fatty acid methyl ester derived from hydrogenated metathesized soybean oil were melted and filled into a reactor under nitrogen gas. Next, 14.6 grams of ethanolamine (i.e., a 1:3 ratio of amine equivalents in the amine to ester equivalents in the FAME) were added under nitrogen at approximately 60° C. The mixture was stirred/homogenized for a few minutes and 0.35 grams of lithium carbonate basic catalyst were added (i.e., 0.5 percent by weight catalyst per FAME). The mixture was stirred and heated to 120-180° C. under nitrogen and held at 120-180° C. for several hours. After the reaction, the mixture was vacuum pumped for 30-60 minutes to drive off the water and unreacted amine. Finally, the resulting wax was decanted out of the flask and tested for physical properties such as drop point, congeal point, and needle penetration (shown below in Table 2).

Example 7

70 grams of fatty acid methyl ester derived from hydrogenated metathesized soybean oil were melted and filled into a reactor under nitrogen gas. Next, 17.4 grams of diethylamine (i.e., a 1:3 ratio of amine equivalents in the amine to ester equivalents in the metathesized natural oil) were added under nitrogen at approximately 60° C. The mixture was stirred/homogenized for a few minutes and 0.35 grams of lithium carbonate basic catalyst were added (i.e., 0.5 percent by weight catalyst per FAME). The mixture was stirred and heated to 120-180° C. under nitrogen and held at 120-180° C. for several hours. After the reaction, the mixture was vacuum pumped for 30-60 minutes to drive off the water and unreacted amine. Finally, the resulting wax was decanted out of the flask and tested for physical properties such as drop point, congeal point, and needle penetration (shown below in Table 2).

Example 8

70 grams of fatty acid methyl ester derived from hydrogenated metathesized soybean oil were melted and filled into a reactor under nitrogen gas. Next, 13.9 grams of hexamethylenediamine (i.e., a 2:3 ratio of amine equivalents in the amine to ester equivalents in the metathesized natural oil) were added under nitrogen at approximately 60° C. The mixture was stirred/homogenized for a few minutes and 0.35 grams of lithium carbonate basic catalyst were added (i.e., 0.5 percent by weight catalyst per FAME). The mixture was stirred and heated to 120-180° C. under nitrogen and held at 120-180° C. for several hours. After the reaction, the mixture was vacuum pumped for 30-60 minutes to drive off the water and unreacted amine. Finally, the resulting wax was decanted out of the flask and tested for physical properties such as drop point, congeal point, and needle penetration (shown below in Table 2).

TABLE 2

Amide waxes produced by FAME amidation

| Example | Amine | Drop Point (° C.) | Congeal Point (° C.) | Needle Penetration (dmm) |
|---|---|---|---|---|
| 5 | Ethylenediamine | 134.1 | 126.0 | 10 |
| 6 | Ethanolamine | 106.7 | 109.0 | 18 |
| 7 | Diethylamine | 40.5 | 40.5 | 55 |
| 8 | Hexamethylenediamine | 128.8 | 111.0 | 13 |

Table 2 shows the results for drop point using the Mettler Drop Point FP80 system, congeal point using ASTM-D938, and needle penetration using ASTM-D1321-02a.

Comparing the physical properties of the waxes in Tables 1 and 2, amidation of hydrogenated metathesized soybean oil produced more waxes with higher drop points than the amidation of the fatty acid methyl esters having no polyfunctional properties. Structure and amino group concentration also play a part in the physical properties of the amidated metathesized natural oils produced. For example, diethylamine (a secondary amine consisting of an amino group with two ethyl group substituents) reacted with the HMSBO to produce a wax with a higher drop point and congeal point than the FAME.

Example 9: Fatty Acid-Amidated Metathesized Natural Oil Blend Study

In this example, HMSBO fatty acid waxes were blended with various concentrations of amidated metathesized natural oil (20 percent by weight amidated metathesized natural oil, 40 percent by weight, 60 percent by weight, and 80 percent by weight). The physical properties of each blend were studied to determine the effects of the amidated metathesized natural oil on the blend. Additional samples of 100% fatty acid wax (i.e., 0 percent by weight amidated metathesized natural oil) and 100% amidated metathesized natural oil were studied as well.

The amidated metathesized natural oil was prepared by adding 700 g HMSBO to a reactor equipped with a stirrer (heavy magnetic stir bar). The HMSBO was stirred and heated in the reactor to 80° C. under nitrogen gas. Next, 72 g ethylenediamine was added to the reactor and stirred/homogenized for a few minutes. Then, 3.5 g sodium carbonate basic catalyst was added as a powder. The mixture was stirred vigorously to keep the catalyst agitated. The reactor was heated to 120° C. and then to 150° C. After 20-30 minutes, the product began to solidify. Therefore, the reactor temperature was increased again to 165° C. to keep the product liquid. The reaction time was at least one hour at elevated temperature (i.e., greater than 140° C.). After the reaction, the mixture was vacuum pumped for at least 30-60 minutes to drive off the water, unreacted amine, and glycerol.

The blends were made by melting the two waxes together at approximately 170° C. Each blend was stirred until it was clear. Each blend, along with the pure samples of amidated metathesized natural oil and HMSBO fatty acid, was tested for drop point (using the Mettler Drop Point FP80 system) and needle penetration (using ASTM-D1321-02a). The results are shown in FIGS. 4 and 5.

In FIG. 4, the drop point graph shows that the addition of the amidated metathesized natural oil increased the drop point compared to the pure HMSBO fatty acid wax. The trend is an increasing drop point up to 60 percent by weight concentration where there is a slight decrease until it gets to 100 percent by weight (pure amidated metathesized natural oil). This effect could be due to some free amino groups present, which give salt-like interactions with carboxylic groups of the HMSBO fatty acids. The highest drop point of 172.3° C. (342.1° F.) was achieved at 40 percent by weight amidated metathesized natural oil, but even at 20 percent by weight amidated metathesized natural oil, there was an increase of about 22° C. (40° F.) from the pure HMSBO fatty acid.

FIG. 5 shows the needle penetration values with increasing amidated metathesized natural oil concentration. The pure distilled fatty acid has a value of 1.5 dmm and the pure amidated metathesized natural oil has a value of 10 dmm. The trend leans toward a softer wax as the amidated metathesized natural oil concentration increases. The optimum penetration value (i.e., hardest wax) of 1 dmm resulted with the 40 percent by weight amidated metathesized natural oil concentration sample.

The results of this study prove that drop point of the pure distilled fatty acid can be manipulated with the addition of the amidated metathesized natural oil. The physical product of a few of the blends (e.g., the 40 percent by weight amidated metathesized natural oil concentration blend) has the shrinkage properties and hardness similar to that of a carnauba or montan wax. The shine or glossiness is another added quality. The optimal blend was observed at 40 percent by weight amidated metathesized natural oil concentration using this particular amidated metathesized natural oil and fatty acid blend. Other amidated metathesized natural oils may also be utilized for blending with the distilled fatty acid.

Example 10: S155-Amidated Metathesized Natural Oil Blend Study

S-155 is a hydrogenated soybean oil sold by Elevance Renewable Sciences, Bolingbrook, Ill. S-155 has potential for use in hot melt adhesive applications. However, the congeal point for the wax is too low by approximately 6° C. (10° F.). In this example, S-155 hydrogenated soybean oil was blended with various concentrations of amidated metathesized natural oil (0.05 percent by weight amidated metathesized natural oil, 0.1 percent by weight, 0.3 percent by weight, 0.5 percent by weight, 1 percent by weight, 2 percent by weight, 3 percent by weight, and 5 percent by weight). The physical properties of each blend were studied to determine the effects of the amidated metathesized natural oil on the blend. Additional samples of 100% S-155 (i.e., 0 percent by weight amidated metathesized natural oil) were studied as well. The amidated metathesized natural oil was prepared according to Example 9. The blends were made by stirring the two waxes together and heating the blend to approximately 170-200° C. It was observed that the resulting blends for the higher concentrations of amidated metathesized natural oil turned into a petroleum-like consistency upon cooling. Each blend, along with the pure samples of S-155, was tested for congeal point (using ASTM-D938) and drop point (using the Mettler Drop Point FP80 system). The results are shown in FIGS. 6 and 7.

In FIG. 6, the congeal point graph shows that the addition of the amidated metathesized natural oil increased the congeal point compared to the pure S-155 hydrogenated soybean oil. With only a 1 percent by weight concentration of amidated metathesized natural oil, the congeal point more than doubled from 52° C. (126° F.) to 129° C. (264.2° F.) and further increased with higher concentrations of amidated metathesized natural oil.

During cooling, the clear melt turned cloudy. This effect increases for higher concentrations. This effect is due to crystallization of the higher melting amidated metathesized natural oil in S-155. These crystallites act as nucleation sites for the S-155 and cause the congeal point to increase. For concentrations below 1 percent by weight amidated metathesized natural oil, the rate at which the congeal point increases gradually. Above 1 percent by weight amidated metathesized natural oil, the change is more abrupt.

Similarly, in FIG. 7, the drop points for lower concentrations of amidated metathesized natural oil (<1 percent by weight) in the wax blend were between 62.3° C. (144.2° F.) and 67.4° C. (153.4° F.). At 1 percent by weight amidated metathesized natural oil concentration and greater, the observed increase in drop point was almost linear. It appeared that the addition of the amidated metathesized natural oil improved some of the brittleness of S-155 without softening it.

The results of this study prove that the congeal point of the pure S-155 can be successfully manipulated with the addition of the amidated metathesized natural oil. An increase in the congeal point by 6° C. (10° F.) in relation to pure S-155 could be achieved with the addition of approximately 0.15-0.20 percent by weight of this particular amidated metathesized natural oil.

Example 11: Additional Amide Wax Blends

Comparable studies were performed with other low melting waxes such as paraffin to observe the increase in the drop point of these materials. The blending of a small amount of amidated metathesized natural oil (produced by reacting ethylenediamine with HMSBO) with natural oils [HMSBO, stearic acid, paraffin, Stable Flake® P oil (a hydrogenated palm oil available from Cargill, Inc., Minneapolis, Minn.)] gives petrolatum-like materials.

| Ethylenediamine/HMSBO wax concentration (wt %) | Host wax | Drop point (° C.) |
|---|---|---|
| 0.0 | HMSBO | 66.0 |
| 0.2 | HMSBO | 65.8 |
| 0.5 | HMSBO | 65.8 |
| 1.0 | HMSBO | 89.3 |
| 2.0 | HMSBO | 118.9 |
| 5.0 | HMSBO | 183.0 |
| 40.0 | Stearic acid | 143.6 |
| 0.0 | Stable Flake ® P | 57.3 |
| 0.2 | Stable Flake ® P | 57.4 |
| 0.5 | Stable Flake ® P | 57.5 |
| 1.0 | Stable Flake ® P | 57.4 |
| 2.0 | Stable Flake ® P | 83 |
| 5.0 | Stable Flake ® P | 151.1 |
| 0.0 | Paraffin | 54.7 |
| 0.2 | Paraffin | 55.4 |
| 0.5 | Paraffin | 55.3 |
| 1.0 | Paraffin | 103.1 |
| 2.0 | Paraffin | 146.3 |

It was observed that the drop point of the amidated metathesized natural oil-natural oil blends increased from 66° C. to 183° C. with the addition of 5 percent by weight amidated metathesized natural oil in the HMSBO. A mere 2 percent by weight addition of amidated metathesized natural oil in HMSBO nearly doubled the drop point from 66° C. to 119° C. Additionally, the addition of amidated metathesized natural oil in Stable Flake® P increased the drop point from 57° C. to 83° C. (2 percent by weight addition) and 151° C. (5 percent by weight addition). Further, the addition of amidated metathesized natural oil in paraffin increased the drop point from 55° C. to 103 (1 percent by weight addition) and 146° C. (2 percent by weight addition).

Example 12: Physical Property/Time Dependency Study

In this example, amidated metathesized natural oils were prepared by reacting ethylenediamine with HMSBO. The reaction time was varied (1 hr, 2 hr, 4 hr, and 6 hr) and the resulting wax products were analyzed.

For each reaction, approximately 50 g HMSBO was added to a reactor flask and placed in an oil bath heated to 100° C. to melt the wax. Nitrogen gas was flushed through the apparatus as the wax was melted. Next, approximately 5.1 g ethylenediamine was added to the reactor and stirred/homogenized for 5 minutes. Then, 0.25 g lithium carbonate basic catalyst was added. The mixture was stirred to agitate the catalyst. The reactor was then heated to approximately 170° C. and held for 1, 2, 4, or 6 hours. After the reaction, the mixture was vacuum pumped for an hour to drive off the water, unreacted amine, and glycerol. Each wax was then tested for physical properties such as drop point (using the Mettler Drop Point FP80 system) and needle penetration value (using ASTM-D1321-02a). The results of the tests are shown in FIGS. 8 and 9.

In FIG. 8, the drop point data shows a slight increase in going from 1 hr to 2 hr. The remaining data is steadier with another slight increase at the 6 hr sample. Therefore, it would be up to the user to choose the appropriate reaction time according to efficiency, production, and cost-effectiveness.

In FIG. 9, the needle penetration data show a hardness range from 4-8 dmm, which is harder than the penetration values for most typical commercial waxes (e.g., 1-4 dmm for hydrogenated natural oils, microcrystalline waxes and natural waxes such as beeswax). The 1 hr and 6 hr samples showed some cracking on the sides. The 4 hr sample was deemed the hardest and showed more glossiness than the other samples. This could be due to its crystal structure that also gives it its hardness. All samples showed the same bilateral shrinkage that carnauba wax displays.

In conclusion, the amine-metathesized natural oil reaction can be done in 1 hr and still achieve a high melting point wax. The addition of an hour or two may further improve wax hardness and increase drop point. In certain embodiments, the reaction time of four hours may provide more optimal properties. However, if the range of drop points achieved is appropriate for the potential application, then a 1 hr reaction setup could consume less time and be more cost-effective.

Example 13

In this example, amidated metathesized natural oils were prepared by reacting ethylenediamine with metathesized soybean oil (MSBO) that has not been hydrogenated. The amidated metathesized natural oil was prepared by adding 70 g MSBO to a reactor, wherein the MSBO was stirred and heated in the reactor to 80° C. under nitrogen gas. Next, 14 g ethylenediamine was added to the reactor and stirred/homogenized for a few minutes. Then, 0.35 g sodium carbonate basic catalyst was added as a powder. The mixture was stirred vigorously to keep the catalyst agitated. The reactor was heated to 170° C. and held at temperature for 4 hours. After the reaction, the mixture was vacuum pumped for at least 30-60 minutes to drive off the water, unreacted amine, and glycerol. Finally, the resulting wax tested for physical properties such as drop point and needle penetration (shown below in Table 3).

Example 14

In this example, amidated metathesized natural oils were prepared by reacting ethanolamine with metathesized soybean oil (MSBO). The amidated metathesized natural oil was prepared by adding 70 g MSBO to a reactor, wherein the MSBO was stirred and heated in the reactor to 80° C. under nitrogen gas. Next, 20 g ethanolamine was added to the reactor and stirred/homogenized for a few minutes. Then, 0.35 g sodium carbonate basic catalyst was added as a powder. The mixture was stirred vigorously to keep the catalyst agitated. The reactor was heated to 170° C. and held at temperature for 4 hours. After the reaction, the mixture was vacuum pumped for at least 30-60 minutes to drive off the water, unreacted amine, and glycerol. Finally, the resulting wax tested for physical properties such as drop point and needle penetration (shown below in Table 3).

TABLE 3

Amide waxes produced by MSBO amidation

| Example | Amine | Color | Drop Point (° C.) | Needle Penetration (dmm) |
|---|---|---|---|---|
| 13 | Ethylenediamine | Pale yellow | 137.2 | 28 |
| 14 | Ethanolamine | Off-white | 85.2 | 47 |

Table 3 shows the results for drop point using the Mettler Drop Point FP80 system and needle penetration using ASTM-D1321-02a. The waxes have comparably high drop points with high penetration values, offering a new kind of material compared to currently commercially available waxes.

Additionally, comparing the physical properties of the amidated metathesized natural oils created from MSBO versus the amidated metathesized natural oils in Tables 1 and 2, amidation of MSBO produced softer waxes than the amide waxes from HMSBO and FAME.

Example 15

In this example, four amidated metathesized natural oil samples were prepared by reacting ethylenediamine with hydrogenated metathesized soybean oil (HMSBO).

For each wax sample, approximately 70 g HMSBO was added to a reactor flask and placed in an oil bath heated to 100° C. to melt the wax. Nitrogen gas was flushed through the apparatus as the wax was melted. Next, approximately 0.43 g ethylenediamine was added to the reactor and stirred/homogenized for a few minutes. Then, approximately 0.35 g sodium carbonate basic catalyst was added. The mixture was stirred to agitate the catalyst and the reactor flask temperature was held at approximately 117° C. for one hour. Then, the temperature was raised to approximately 160-170° C. for 1, 2, 3, and 4 hours for the four samples, respectively.

After the allotted reaction time, the wax product was distilled under vacuum pressure utilizing a trap submerged in liquid nitrogen for one hour at 200° C. Finally, each wax tested for physical properties such as drop point using the Mettler Drop Point FP80 system and needle penetration using ASTM-D1321-02a (shown below in Table 4).

TABLE 4

Amide waxes produced by HMSBO amidation with ethylenediamine

| Example | Yield (%) | Reaction time (hr) | Drop Point (° C.) | Needle Penetration (dmm) | Color |
|---|---|---|---|---|---|
| 15-1 | 96.7 | 1 | 98.1 | 7 | Cream |
| 15-2 | 91.8 | 2 | 99.9 | 6 | Cream |
| 15-3 | 95.3 | 3 | 102.7 | 10 | Cream |
| 15-4 | 92.3 | 4 | 94.4* | — | Sandy brown* |

The results from these tests showed that the ethylenediamine reaction with HMSBO could be conducted in as little as one hour to produce a sample that has a drop point approximately 100° C. Additionally, the results showed that the drop point and needle penetration increased slightly based upon the extent of the reaction time from 1 to 3 hours. It is noted that Example 15-4 produced a lower drop point than expected and sandy brown color due to poor pumping/low flow of nitrogen.

Example 16

In this example, three amidated metathesized natural oil samples were prepared by reacting diethanolamine with hydrogenated metathesized soybean oil (HMSBO) in a similar manner to Example 15. However, in this example, the amine was added directly to the flask before the HMSBO was melted.

For each wax sample, approximately 70 g HMSBO was added to a reactor flask with approximately 10 g diethanolamine. The flask was placed in an oil bath and heated to 100° C. to melt the mixture. Nitrogen gas was flushed through the apparatus as the mixture was melted. Then, approximately 0.35 g sodium carbonate basic catalyst was added. The reactor flask temperature was raised to approximately 190° C. for 12, 14, and 16 hours for the three samples, respectively.

After the allotted reaction time, the wax product was distilled under vacuum pressure utilizing a trap submerged in liquid nitrogen for one hour at 200° C. Finally, the drop point for each wax was tested using the Mettler Drop Point FP80 system (shown below in Table 5).

TABLE 5

Amide waxes produced by HMSBO amidation with diethanolamine

| Example | Yield (%) | Reaction time (hr) | Drop Point (° C.) | Color |
|---|---|---|---|---|
| 16-1 | 90.1 | 12 | 77.8 | Tan |
| 16-2 | 86.5 | 14 | 92.0 | Tan |
| 16-3 | 88.7 | 16 | 82.6 | Tan |

The results from these tests showed a higher drop point for the 14 hr reaction time, but it also has less of a yield than the 12 and 16 hour reactions. In certain embodiments, the reaction time should be 12 hours or less if a lower drop point is also desired (and possibly higher yield).

Diethanolamine has three groups that can react with the ester functionalities of the HMSBO. The amino group reacts first due to its higher nucleophilic character. The hydroxyl groups need more reaction time and deliver a higher cross-linked product. The DEA-HMSBO samples produced in this example report are in the medium range of drop points/viscosity.

Example 17—Hand and Body Moisturizing Lotion

In this example, the amidated metathesized natural oil composition produced by the amine-metathesized natural oil reaction can be blended with additional components to form a hand and body moisturizing lotion. Use of such an amidated metathesized natural oil composition in a hand or body lotion may provide an improved viscosity (i.e., an improved texture during application of the lotion). In this example, the amidated metathesized natural oil composition is produced by reacting diethanolamine with HMSBO.

The hand and body moisturizing lotion contains the following ingredients:

| Ingredient | Wt % |
| --- | --- |
| Phase A | |
| Water | 77.6 |
| Glycerin | 5.0 |
| Cetyl Alcohol | 3.0 |
| Amidated metathesized natural oil | 2.0 |
| *Butyrospermum Parkii* (Shea) Butter | 2.0 |
| *Mangifera Indica* (Mango) Seed Butter | 2.0 |
| *Theobroma Cacao* (Cocoa) Seed Butter | 2.0 |
| Mineral Oil | 2.0 |
| Phase B | |
| Polyacrylamide (and) C13-14 Isoparaffin (and) Laureth-7 | 4.0 |
| Phase C | |
| DMDM Hydantoin | 0.4 |

The lotion is prepared by heating the water and glycerin to about 80° C. and then adding the other ingredients for Phase A. The Phase A materials are mixed until the vegetable butters are completely melted. Next, the mixture is cooled, the Phase B material is added, and mixer speed is increased as the batch thickens. Sufficient mixer speed is maintained to provide good top to bottom mixing during the cooling. When the batch is cooled to below 50° C., Phase C is added. The mixing is continued until the batch reaches room temperature.

Example 18—Lip Balm

In this example, the amidated metathesized natural oil composition produced by the amine-metathesized natural oil reaction can be blended with additional components to form a lip balm. Use of such an amidated metathesized natural oil composition in a lip balm may provide an improved hardness and applicability over current lip balm waxes. In this example, the amidated metathesized natural oil composition is produced by reacting ethylenediamine with HMSBO.

The lip balm contains the following ingredients:

| Ingredient | Wt % |
| --- | --- |
| *Helianthus Annuus* (Sunflower) Seed Oil | 36.0 |
| *Persea Gratissima* (Avocado) Oil | 7.0 |
| *Theobroma Cocao* (Cocoa) Seed Butter | 6.0 |
| Cetearyl Alcohol | 18.0 |
| Amidated metathesized natural oil | 6.0 |
| Hydrogenated Soybean Polyglycerides (and) C15-23 Alkane | 12.0 |
| *Butyrospermum Parkii* (Shea Butter) | 15.0 |

The lip balm is prepared by combining all of the ingredients in a suitable mixing vessel and heating the mixture to about 70° C. As the mixture begins to melt, the mixture is stirred and heated until the batch is completely liquefied and homogeneous. Then, the mixture is poured into containers while hot and allowed to solidify.

Example 19—Hair Pomade

In this example, the amidated metathesized natural oil composition produced by the amine-metathesized natural oil reaction can be blended with additional components to form a hair pomade. In this example, the amidated metathesized natural oil composition is produced by reacting ethylenediamine with HMSBO.

The hair pomade contains the following ingredients:

| Ingredient | Wt % |
| --- | --- |
| Hydrogenated Soybean Oil (and) Hydrogenated Soybean Polyglycerides (and) C15-23 Alkane | 60.00 |
| Amidated metathesized natural oil | 10.00 |
| Mineral Oil | 11.85 |
| Isopropyl Palmitate | 8.00 |
| Lanolin | 5.00 |
| *Persea Gratissima* (Avocado) Oil | 1.50 |
| Tocopherol Acetate | 0.50 |
| BHT | 0.05 |
| Propylene Glycol | 3.00 |
| Propylparaben | 0.10 |

The hair pomade is prepared by combining all of the ingredients in a suitable mixing vessel and heating the mixture to about 70° C. As the mixture begins to melt, the mixture is stirred and heated until the batch is completely liquefied and homogeneous. Then, the mixture is poured into containers while hot and allowed to solidify.

Example 20—Sunscreen Stick

In this example, the amidated metathesized natural oil composition produced by the amine-metathesized natural oil reaction can be blended with additional components to form a sunscreen stick. In this example, the amidated metathesized natural oil composition is produced by reacting ethylenediamine with HMSBO.

The sunscreen stick contains the following ingredients:

| Ingredient | Wt % |
| --- | --- |
| Phase A | |
| Cetearyl Alcohol | 27.0 |
| *Butyrospermum Parkii* (Shea) Butter | 2.0 |
| Amidated metathesized natural oil | 7.0 |
| Cera Alba (Beeswax) | 7.0 |
| C30-45 Alkyl Methicone (and) C30-45 Olefin | 3.0 |
| Phase B | |
| Caprylic/Capric Triglyceride | 21.0 |
| C12-15 Alkyl Benzoate | 18.0 |
| Octocrylene | 7.0 |
| Octyl Salicylate | 5.0 |
| Butyl Methoxydibenzoylmethane | 3.0 |

The sunscreen stick is prepared by combining all of the ingredients for Phase A in a suitable mixing vessel and heating the mixture to about 70° C. In a separate mixing vessel, the ingredients for Phase B are combined and heated to about 60° C. with gentle mixing until the butyl methoxydibenzoylmethane is completely dissolved and the mixture is homogeneous. Phase B is added to Phase A and mixed until homogeneous. Then, the mixture is poured into stick molds while hot and allowed to cool to room temperature.

Example 21—Lipstick

In this example, the amidated metathesized natural oil composition produced by the amine-metathesized natural oil reaction can be blended with additional components to form a lipstick. In this example, the amidated metathesized natural oil composition is produced by reacting ethylenediamine with HMSBO.

The lipstick contains the following ingredients:

| Ingredient | Wt % |
| --- | --- |
| Phase A | |
| Hydrogenated Soybean Polyglycerides (and) C15-23 Alkane | 3.00 |
| Microcrystalline Wax | 4.50 |
| Amidated metathesized natural oil | 11.50 |
| Ceresin | 2.00 |
| Hydrogenated Soybean Oil | 4.50 |
| Isopropyl Myristate | 15.00 |
| Isododecane | 16.20 |
| Octyldodecanol | 7.00 |
| Phase B | |
| *Ricinus Communis* (Castor) Seed Oil | 29.50 |
| Iron Oxides (Yellow/Black blend) | 0.50 |
| Titanium Dioxide | 6.00 |
| Acid Red 92 | 0.20 |
| Pigment Red 57 | 0.10 |

The lipstick is prepared by combining all of the ingredients for Phase B in a ball mill and grinding/mixing the ingredients until the pigments and dyes are dispersed and the mixture is homogeneous. The ingredients for Phase A (except for the isododecane) are combined in a suitable mixing vessel and heated to about 70° C. The ingredients are mixed gently until melted and then added to the Phase B, where the ingredients are then mixed until uniform. The mixture is then cooled. As soon as the mixture cools to about 5 degrees above the solidification temperature, the cooling process is stopped and the isododecane is added. Next, the batch is mixed until uniform and then poured into molds and allowed to cool to room temperature.

Example 22—Sunscreen

In this example, the amidated metathesized natural oil composition produced by the amine-metathesized natural oil reaction can be blended with additional components to form a sunscreen. In this example, the amidated metathesized natural oil composition is produced by reacting diethanolamine with HMSBO.

The sunscreen contains the following ingredients:

| Ingredient | Wt % |
| --- | --- |
| Phase A | |
| Ethylhexyl Methoxycinnamate | 4.0 |
| Caprylyl Methicone | 11.5 |
| Isodecyl Neopentanoate | 7.0 |
| Amidated metathesized natural oil | 2.0 |
| Lauryl PEG/PPG-18/18 Methicone | 2.0 |
| Phase B | |
| Water | 69.0 |
| Sodium Chloride | 1.0 |
| Propylene Glycol | 3.5 |

The sunscreen is prepared by combining all of the ingredients in a mixing vessel. The Phase A ingredients are then heated to 70-80° C. to melt the wax. The ingredients are mixed to disperse the wax into the oil. The ingredients for Phase B are combined in a separate container, heated to the same temperature as Phase A, and mixed until a homogenous mixture is obtained. Phase B is then combined with Phase A with turbulent mixing. The mixer speed must be sufficient to rapidly incorporate Phase B into the batch as it is added. The emulsion will thicken as Phase B is added so the mixer speed must be increased during the addition to maintain good agitation. After all of Phase B has been added, the mixing is continued while the batch is cooled to room temperature.

Example 23

A series of simple emulsions were made with the polar amidated metathesized natural oil to illustrate the emulsification and thickening performance with a variety of cosmetic oils. Emulsion formulations intended for skin care applications like hand and body lotions or creams usually contain ingredients (thickeners) to increase the viscosity of the emulsion formulation. Thickeners are necessary to provide the formulation with the texture and consistency that consumers expect for creams and lotions. For example, a lotion should be pourable, but not runny; a cream should be thicker than a lotion with a the consistency of a soft solid. Thickening the formulation provides the additional advantage of improving the stability of the formulation. When comparing thickeners for relative efficacy, a common approach is to add the different thickeners to a simple emulsion formulation and then measure the viscosity of the emulsions. More efficacious thickeners will produce higher emulsion viscosities compared to less efficacious thickeners.

The emulsions were prepared by first heating the water to about 80° C. In a separate mixing vessel, the cosmetic oil and the polar amidated metathesized natural oil were heated to about 70° C. in a hot water bath and mixed using a dual blade mixer (turbine blade at the end of the mixer shaft with a propeller blade mounted 2 cm above). The oil and polar amidated metathesized natural oil were mixed at about 500 rpm while the hot water was slowly added. After all of the water was added, the mixer was stopped and the walls of the mixing vessel were scraped with a metal spatula to remove any material that was not dispersed into the batch. The heating bath was removed and the mixer speed was increased to about 800 rpm. The batch was then mixed for 30 minutes while it cooled.

The viscosity of the emulsion was measured about 24 hours after they were made using a Brookfield viscometer, model RVDVII+ equipped with a helipath stand. A number 93 "T" spindle and a speed setting of 10 rpm were used.

| Cosmetic Oil | Example 23A | Example 23B | Example 23C | Example 23D | Example 23E | Example 23F |
| --- | --- | --- | --- | --- | --- | --- |
| Isopropyl Palmitate | 5.0 | | | | | |
| Caprylic/Capric Triglyceride | | 5.0 | | | | |
| Dicaprylyl Carbonate | | | 5.0 | | | |
| Mineral Oil | | | | 5.0 | | |

-continued

| Cosmetic Oil | Example 23A | Example 23B | Example 23C | Example 23D | Example 23E | Example 23F |
|---|---|---|---|---|---|---|
| Phenyl Trimethicone | | | | | 5.0 | |
| Dimethicone | | | | | | 5.0 |
| Polar amidated metathesized natural oil | 5.0 | 5.0 | 5.0 | 5.0 | 5.0 | 5.0 |
| Water | 90.0 | 90.0 | 90.0 | 90.0 | 90.0 | 90.0 |
| Viscosity (cP) | 28,880 | 24,680 | 19,880 | 23,040 | 18,180 | 13,620 |

Comparative Examples 23G-23L

Comparative examples were made with a commercial product, Arlacel 165, which is a mixture of glyceryl stearate and PEG-100 stearate supplied by Croda Incorporated. The same procedure was used to prepare these emulsions. These emulsions were stable, but much lower in viscosity compared to the emulsions prepared with the polar amidated metathesized natural oil. It was difficult to measure the viscosity of these emulsions using the same spindle and speed on the Brookfield viscometer. Larger spindles were used (No. 92 or 91) with higher speeds in an attempt to obtain an accurate viscosity reading, but the reported values are estimates.

| Cosmetic Oil | Comp. Example 23G | Comp. Example 23H | Comp. Example 23I | Comp. Example 23J | Comp. Example 23K | Comp. Example 23L |
|---|---|---|---|---|---|---|
| Isopropyl Palmitate | 5.0 | | | | | |
| Caprylic/Capric Triglyceride | | 5.0 | | | | |
| Dicaprylyl Carbonate | | | 5.0 | | | |
| Mineral Oil | | | | 5.0 | | |
| Phenyl Trimethicone | | | | | 5.0 | |
| Dimethicone | | | | | | 5.0 |
| Arlacel 165 | 5.0 | 5.0 | 5.0 | 5.0 | 5.0 | 5.0 |
| Water | 90.0 | 90.0 | 90.0 | 90.0 | 90.0 | 90.0 |
| Viscosity (cP) | 40 | 43 | 32 | 64 | 40 | 77 |

Comparative Examples 23M-23R

Comparative examples were made with a commercial product, Lipowax D, which is a mixture of cetearyl alcohol and ceteareth-20 supplied by Lipo Chemicals. The same procedure used for the previous examples was used to make a series of emulsions with Lipowax D. These emulsions were somewhat thicker than the emulsions made with Arlacel 165, but not as thick as the emulsions made with the polar amidated metathesized natural oil.

| Cosmetic Oil | Comp. Example 23M | Comp. Example 23N | Comp. Example 23O | Comp. Example 23P | Comp. Example 23Q | Comp. Example 23R |
|---|---|---|---|---|---|---|
| Isopropyl Palmitate | 5.0 | | | | | |
| Caprylic/Capric Triglyceride | | 5.0 | | | | |
| Dicaprylyl Carbonate | | | 5.0 | | | |
| Mineral Oil | | | | 5.0 | | |
| Phenyl Trimethicone | | | | | 5.0 | |
| Dimethicone | | | | | | 5.0 |
| Lipowax D | 5.0 | 5.0 | 5.0 | 5.0 | 5.0 | 5.0 |
| Water | 90.0 | 90.0 | 90.0 | 90.0 | 90.0 | 90.0 |
| Viscosity (cP) | 8,320 | 6,340 | 7,020 | 2,470 | 6,880 | 5,690 |

Comparative Example 23S

A comparative example was made by synthesizing diethanolamine amide wax from S-155. Fully hydrogenated soybean oil (S-155) was mixed with 13.7 wt % diethanolamine (DEA) and heated under nitrogen to 80° C. until molten. Sodium carbonate (0.5 parts by weight compared to the amount of S-155) was added during stirring. The temperature was raised to 160° C. for 16 hours. Volatiles were removed under vacuum. The DEA amide wax had a measured drop point of 59.1° C. (138.3° F.).

After the wax cooled down, emulsions were prepared using a simple single oil formulation consisting of 5% wax, 5% oil, and 90% water (as discussed above in Example 23). The results showed that in this comparative example, the S-155 derived DEA amide wax gave gelatinous curds and did not form a stable emulsion with silicon oil (dimethicone) compared to metathesized DEA wax in Example 23. A second test emulsion made from the DEA S-155 amide wax with caprylic/capric triglyceride gave an emulsion with a viscosity of 8100 cP compared to around 25000 cP for the metathesized equivalent.

This comparative example shows the superior emulsion properties of metathesized versus non-metathesized hydrogenated DEA amide wax.

Example 24—Pigment Stick

When dispersed into cosmetic oils, the amidated metathesized natural oil may provide a structuring effect. Structurants may be used to make products such as lipsticks or antiperspirant sticks. The structuring performance of amide wax was tested by making the following formulation. Various waxes ("test wax") were included in the formulation to determine the effect on hardness:

| Ingredient | Wt % |
| --- | --- |
| Cetearyl Alcohol | 17.0 |
| Phenyl Trimethicone | 15.0 |
| "Test wax" | 5.0 |
| Cyclopentasiloxane | 38.0 |
| Pigment Blend (mixture of titanium dioxide and iron oxides to give desired color) | 25.0 |

The waxes were prepared by mixing the first three ingredients in a vessel, heating the mixture to 70-80° C., and gently mixing until the cetearyl alcohol and test wax were melted. In a separate mixing vessel, the pigment blend was dispersed into the cyclopentasiloxane. Then, the pigment dispersion was blended into the hot wax mixture and the heating was maintained to prevent solidification of the wax. As soon as all of the pigment dispersion has been added, the wax was cooled and poured into suitable molds (4 oz wide-mouth glass jar) before the formulation hardened. The wax was allowed to stand for 24 hours before any measurements were taken.

A Texture Analyzer, model TA XT Plus, manufactured by Stable Micro Systems was used to test the hardness of the formulations. This instrument has a movable arm equipped with force sensors that is programmed to push a probe into the sample and record the resistance to penetration as the probe is pushed into the sample. A 45° conical stainless steel probe (TA15) was pushed into the sample at a rate of 0.5 mm/sec to a depth of 10 mm below the surface of the sample. The peak (maximum) force recorded by the instrument was taken as a measure of the hardness of the sample.

The table below gives the hardness results for several test waxes:

| Test Wax | Peak Force (kg) |
| --- | --- |
| Carnauba wax | 1.06 |
| HMSBO | 0.29 |
| Amide wax (0.6 wt % ethylenediamide in HMSBO, 106° C. drop point) | 1.16 |
| Amide wax (6 wt % ethanolamine, 10 wt % diethanolamine, and 1 wt % ethylenediamine in HMSBO, 87° C. drop point, 4.6 dmm) | 0.76 |

It is noted that the amide waxes produced improved peak force hardness over the HMSBO mixture, and produced similar peak force hardness results to the carnauba wax mixture.

Example 25—Lipstick Base

The structuring effect of amide wax was evaluated in a second anhydrous formulation, a lipstick base. A lipstick base is a mixture of oils, waxes, and pigments to which various oil-soluble dyes can be added to produce the desired lipstick color. The structuring performance of amide wax was tested by making the following formulations. Various waxes ("test wax") were included in the formulation to determine the effect on hardness.

| Ingredient | Wt % |
| --- | --- |
| Phase A | |
| Ozokerite | 4.0 |
| "Test Wax" | 16.0 |
| Octyldodecanol | 25.0 |
| HMSBO | 4.0 |
| Lanolin oil | 9.0 |
| Soybean oil | 2.0 |
| Oleyl alcohol | 8.0 |
| Phase B | |
| Cyclopentasiloxane (and) Polypropylsilsesquioxane (Dow Corning ® 670 Fluid) | 5.0 |
| Cyclopentasiloxane | 20.9 |
| Iron Oxide (red) | 4.7 |
| Titanium Dioxide | 1.4 |

The waxes were prepared by mixing the ingredients for Phase A in a vessel, heating the mixture to 70-80° C., and gently mixing until all of the waxes have melted. In a separate mixing vessel, the ingredients for Phase B were blended using a high shear mixer to fully disperse the pigments. The pigment dispersion (Phase B mixture) was then blended into the hot Phase A mixture and the heat was maintained to prevent solidification of the wax. As soon as all of Phase B had been added, the combined mixture was stirred until homogeneous. Then, the mixture was cooled, and poured into suitable molds before the formulations hardened.

The hardness of the lipstick base samples was measured in the same fashion as the pigment stick (described in the previous example), but because of the tendency of the lipstick base to crack, the penetration depth was reduced to 5 mm. This produces lower peak force measurements compared to the pigment stick, but still allows the structuring effect produced by different waxes to be compared.

The following table summarizes the results for several waxes:

| Test Wax | Peak Force (kg) |
| --- | --- |
| Candelilla wax | 0.173 |
| Amide wax (12 wt % ethanolamine and 1 wt % ethylenediamine in HMSBO, 104° C. drop point, 2.6 dmm) | 0.171 |
| Amide wax (0.6 wt % ethylenediamine in HMSBO, 106° C. drop point) | 0.121 |

It is noted that the amide waxes produced similar peak force hardness results to the candelilla wax mixture.

Example 26—Leveling Agent for Anticorrosion Application

In this example, the amidated metathesized natural oil composition produced by reacting ethylene diamine (EDA) with HMSBO can be powderized and used as a leveling agent. In this example, the powderized amide wax was used as a leveling agent in a wax coating (Ca soaps of MSBO) for an anticorrosion application. The EDA amide wax was introduced as a fine powder in a 1 wt % loading level. The surface of the coating was improved and small bubbles, which tend to form in the coating during heating, were prevented by the additive.

What is claimed is:

1. A wax composition comprising:
an amidated metathesized natural oil formed from a metathesized natural oil and at least one amine, wherein the amidated metathesized natural oil comprises molecules having the following structures:

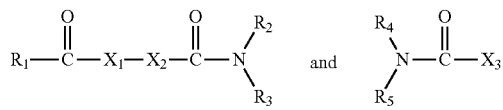

wherein $R_1$ is

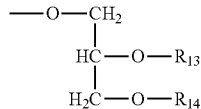

wherein $R_2$, $R_3$, $R_4$, and $R_5$, are independently selected from the group consisting of hydrogen, alcohols, alkyls, aryls, alkyl-amines, aryl-amines, ether amines, amino acids and esters, thiol amines, ureas, and thioureas,
wherein $R_{10}$ and $R_{11}$ are independently selected from the group consisting of:
hydrogen and

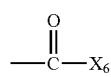

wherein $X_1$, $X_2$, $X_3$, and $X_6$ are independently selected from the group consisting of $C_4$-$C_{28}$ saturated or unsaturated alkyl chains from either a fatty acid of a natural oil, or a derivative thereof formed by a metathesis reaction.

2. The wax composition of claim 1, wherein the metathesized natural oil is a hydrogenated metathesized natural oil.

3. The wax composition of claim 2, wherein the hydrogenated metathesized natural oil is selected from the group consisting of hydrogenated metathesized vegetable oil, hydrogenated metathesized algal oil, hydrogenated metathesized animal fat, hydrogenated metathesized tall oil, hydrogenated metathesized derivatives of these oils, and mixtures thereof.

4. The wax composition of claim 1 having a drop point between 70° C. and 200° C., and a hardness between 1 dmm and 40 dmm as measured by needle penetration.

5. The wax composition of claim 1 having a drop point that is greater by at least 10° C. than the drop point of a second metathesized natural oil composition similar in all respects except that the second metathesized natural oil composition is not amidated.

6. The wax composition of claim 1, wherein the amidated metathesized natural oil is blended with a natural oil composition to form an amidated metathesized natural oil-natural oil blend; wherein the amidated metathesized natural oil comprises between 0.1 percent by weight and 10 percent by weight of the wax composition; wherein the drop point of the amidated metathesized natural oil-natural oil blend is greater than the drop point of the natural oil composition by at least 5° C.

7. The wax composition of claim 1, wherein the wax is used in an application selected from the group consisting of: an emulsifying wax application, a binder of cosmetics, a hardness modifier application, a thickening agent application, a wetting agent application, a foam stabilizer application, a polish application, a coating application, a structurant application, a structurant or nucleating agent for a cosmetic or adhesive application, a pigment carrier application, a sunscreen stick application, a hair pomade application, or a hand/body lotion application.

8. The wax composition of claim 7, having between 1 percent by weight and 15 percent by weight amidated metathesized natural oil in the application.

9. The wax composition of claim 1 further comprising a hydroxy-metathesis oligomer having the following structure:

wherein $R_{12}$ is:

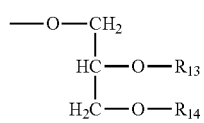

wherein $R_{13}$ and $R_{14}$ are independently selected from the group consisting of:
hydrogen and

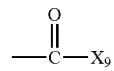

wherein $X_9$ is selected from the group consisting of $C_4$-$C_{28}$ saturated or unsaturated alkyl chains from either a fatty acid of a natural oil, or a derivative thereof formed by a metathesis reaction.

10. A method of making an amidated metathesized natural oil comprising:
providing an amine;
providing a metathesized natural oil;
mixing the amine and the metathesized natural oil in the presence of a basic catalyst or heat, causing a reaction between the amine and metathesized natural oil, therein forming the amidated metathesized natural oil.

11. The method of claim 10, wherein the mixing is conducted in the presence of the basic catalyst selected from the group consisting of: sodium carbonate, lithium carbonate, sodium methanolate, potassium hydroxide, sodium hydride, potassium butoxide, potassium carbonate, or a mixture thereof.

12. The method of claim 10, wherein the ratio of amine equivalents in the amine to ester equivalents in the metathesized natural oil is between 1:100 and 10:1.

13. The method of claim 10, wherein the amount of the basic catalyst is between 0.1 percent by weight and 10 percent by weight of the metathesized natural oil.

14. The method of claim 10, wherein the mixing is conducted in an inert atmosphere.

15. The method of claim 10, wherein the reaction is conducted at a temperature between 80° C. and 250° C.

16. The method of claim 10 further comprising vacuum-pumping the wax composition to separate at least one of the following: water, unreacted amine, glycerol, or paraffinic compounds.

17. The method of claim 10 further comprising epoxidizing the amidated metathesized natural oil with a peroxyacid.

18. The method of claim 10, wherein the metathesized natural oil is hydrogenated before mixing with the amine.

19. The method of claim 10, wherein the metathesized natural oil is selected from the group consisting of metathesized vegetable oil, metathesized algae oil, metathesized animal fat, metathesized tall oil, metathesized derivatives of these oils, and mixtures thereof.

20. The method of claim 10, further comprising blending the amidated metathesized natural oil with a natural oil composition to form an amidated metathesized natural oil-natural oil blend, wherein the amidated metathesized natural oil-natural oil blend has between 0.1 percent by weight and 10 percent by weight of the amidated metathesized natural oil; and wherein the drop point of the amidated metathesized natural oil-natural oil blend is greater than the drop point of the natural oil composition by at least 5° C.

* * * * *